US008614466B2

(12) United States Patent
Rasooly et al.

(10) Patent No.: US 8,614,466 B2
(45) Date of Patent: Dec. 24, 2013

(54) SEMICONDUCTOR FOR MEASURING BIOLOGICAL INTERACTIONS

(75) Inventors: Avraham Rasooly, Silver Spring, MD (US); Minghui Yang, Milwaukee, WI (US); Hugh A. Bruck, Wheaton, MD (US); Yordan Kostov, Columbia, MD (US)

(73) Assignees: The United States of America, as Represented by the Secretary, Department of Health and Human Services, Washington, DC (US); University of Maryland, Baltimore County, Baltimore, MD (US); University of Maryland, College Park, College Park, MD (US)

( * ) Notice: Subject to any disclaimer, the term of this patent is extended or adjusted under 35 U.S.C. 154(b) by 215 days.

(21) Appl. No.: 13/128,851

(22) PCT Filed: Nov. 18, 2009

(86) PCT No.: PCT/US2009/064938
§ 371 (c)(1),
(2), (4) Date: May 11, 2011

(87) PCT Pub. No.: WO2010/059687
PCT Pub. Date: May 27, 2010

(65) Prior Publication Data

US 2011/0217763 A1 Sep. 8, 2011

Related U.S. Application Data

(60) Provisional application No. 61/115,846, filed on Nov. 18, 2008.

(51) Int. Cl.
*H01L 29/772* (2006.01)

(52) U.S. Cl.
USPC ................ 257/253; 257/E29.242; 257/E21.4; 438/48; 435/287.1; 977/742; 977/734

(58) Field of Classification Search
USPC ............................... 257/253, E29.242, E21.4
See application file for complete search history.

(56) References Cited

U.S. PATENT DOCUMENTS 6,918,284 B2 7/2005 Snow et al.
7,385,267 B2 6/2008 Lieber et al.

(Continued)

FOREIGN PATENT DOCUMENTS

WO WO 02/33732 A2 4/2002
WO WO 2006/042276 A2 4/2006

OTHER PUBLICATIONS

European search report from EP 09828144.7-2404 / 2350644 PCT/US2009064938, Mar. 7, 2012, 5 pages.
Bekyarova et al., "Applications of Carbon Nanotubes in Biotechnology and Biomedicine," *J Biomed Nanotechnol.* Mar. 1, 2005, 31 pages.

(Continued)

*Primary Examiner* — Mamadou Diallo
(74) *Attorney, Agent, or Firm* — Klarquist Sparkman, LLP

(57) ABSTRACT

An apparatus and method are disclosed for electrically directly detecting biomolecular binding in a semiconductor. The semiconductor can be based on electrical percolation of nanomaterial formed in the gate region. In one embodiment of an apparatus, a semiconductor includes first and second electrodes with a gate region there between. The gate region includes a multilayered matrix of electrically conductive material with capture molecules for binding target molecules, such as antibody, receptors, DNA, RNA, peptides and aptamer. The molecular interactions between the capture molecules and the target molecules disrupts the matrix's continuity resulting in a change in electrical resistance, capacitance or impedance. The increase in resistance, capacitance or impedance can be directly measured electronically, without the need for optical sensors or labels. The multi-layered matrix can be formed from a plurality of single-walled nanotubes, graphene, or buckeyballs or any kind of conductive nanowire, such as metal nanowires or nanowires made from conductive polymers.

30 Claims, 14 Drawing Sheets

(56) References Cited

U.S. PATENT DOCUMENTS

| | | | | |
|---|---|---|---|---|
| 7,399,400 | B2 | 7/2008 | Soundarrajan et al. | |
| 2001/0053535 | A1 | 12/2001 | Bashir et al. | |
| 2003/0102510 | A1 | 6/2003 | Lim et al. | |
| 2003/0134433 | A1 | 7/2003 | Gabriel et al. | |
| 2006/0154489 | A1 | 7/2006 | Tornow et al. | |
| 2008/0283875 | A1 | 11/2008 | Mukasa et al. | |
| 2009/0208922 | A1 * | 8/2009 | Choi et al. | 435/4 |

OTHER PUBLICATIONS

Kim et al., "Carbon Nanotubes for Electronic and Electrochemical Detection of Biomolecules," *Adv Mater Deerfield*, Oct. 19, 2007, pp. 3214-3228.

Upadhyayula et al., "Single-Walled Carbon Nanotubes as Fluorescence Biosensors for Pathogen Recognition in Water Systems," *Research Letters in Nanotechnology*, vol. 2008, Article ID 156358, 2008, 5 pages.

* cited by examiner

SEMICONDUCTOR FOR MEASURING BIOLOGICAL INTERACTIONS

CROSS REFERENCE TO RELATED APPLICATIONS

This is the U.S. National Stage of International Application No. PCT/US2009/064938, filed Nov. 18, 2009, which was published in English under PCT Article 21(2), which in turn claims the benefit of U.S. Provisional Application No. 61/115,846, filed Nov. 18, 2008. The provisional application is incorporated herein in its entirety.

FIELD

The present application relates to semiconductors, and, particularly, to electrical detection of biomolecules in a semiconductor.

BACKGROUND

Biological semiconductors (BSC) are electronic components that change conductivity based upon biological interactions, such as protein-protein interactions, DNA-protein binding, nucleic acid binding, and hormone-receptor binding. The ability to directly measure such biological interactions has scientific, medical, and industrial applicability.

Nanomaterials are increasingly being adapted for biosensing. Once such nanomaterial can be fabricated using single-walled carbon nanotubes (SWNT). The SWNTs are molecular wires with unique electrical properties attractive for solid-state nanoelectronics including logic gates, digital memory, digital switching and integration into logic circuits transistor arrays. Individual SWNTs are quantum wires so their conductivity depends on how conduction electrons interact with the atoms within the SWNTs. The electrical conductance of a single nanotube was shown to be highly sensitive to its environment, and varies significantly with changes in electrostatic charges and surface adsorption of many molecules. Using chemical vapor deposition (CVD) to grow individual tubes, it was shown that there is a large conductance change in response to the electrostatic, chemical and biological molecules when they are utilized as gates for field-effect transistors (FETs) chemical and biological sensors. In addition to this semiconductor effect for an individual tube, SWNTs interconnected in a submonolayer network (also fabricated by CVD) were shown to exhibit semiconductor-like behavior in which the conductance can be gated and surface interactions with biomolecules can be used for biosensing.

Unfortunately, the method of FET fabrication using individual or submonolayer networks of SWNTs is complex and requires on-chip SWNTs synthesis for each FET, making it particularly difficult for fabricating multi-FET chips. Additionally, CVD fabrication is expensive and requires special expertise. For these reasons, fabricating FETs using SWNTs has been very limited.

It is desirable, therefore, to provide a biological semiconductor that is relatively simple to fabricate (especially for multi-gate devices) and can be made at low cost.

SUMMARY

An apparatus and method are disclosed for electrically detecting biomolecular binding in a semiconductor. The apparatus and method take advantage of a physical principle called “electrical percolation,” which relates to the flow of electricity through a random resistive network. The passage of current through the network depends on the network’s continuity, which can be varied based on the detection and/or quantity of an analyte in a biological sample.

In one embodiment of an apparatus, a semiconductor includes first and second electrodes with a gate region there between. The gate region includes a multi-layered network of electrically conductive material with capture biomolecules for binding target biomolecules. The network can be within a three-dimensional matrix. This allows capture biomolecules to be positioned internally within the matrix and on an outer surface of the matrix. The molecular interactions between the capture biomolecules and the target biomolecules within the matrix disrupts the network’s continuity resulting in increased electrical resistance, capacitance or impedance. Such changes in continuity can be directly measured using electrical resistance sensors (e.g., ohm meter) or any other electrical sensors for measuring voltage, current, capacitance or impedance, for direct detection without the need for optical sensors or labels. Thus, biomolecular binding (e.g., antibody/antigen) changes the conductive properties of a semiconductor, which allows for a simple and direct mechanism for detection of biomolecular interactions.

The multi-layered network can be formed by depositing of a variety of carbon-based materials, such as carbon nanotubes (CNT), graphene, or buckeyballs or using any metallic nanowires or conductive polymer nanowires. The semiconductors can be fabricated at or near the percolation threshold. At the percolation threshold, small changes in the molecular complexes can result in large changes in conductivity increasing the sensitivity of detection.

In one embodiment of a method of use, biomolecular interactions are detected using the semiconductor. A sample (such as a liquid sample) can be introduced, which can include target biomolecules to be detected. If the target biomolecules present in the sample are introduced into the semiconductor, a binding pair is formed between a capture biomolecule and the target biomolecule. The binding pair changes a resistance in the gate region of the semiconductor by disrupting the continuity of the network. An automatic measurement of resistance can then be performed in order to detect the biomolecular interactions. A quantitative determination of biomolecular activity can be made based on a comparison between the measured resistance and a control resistance measurement.

In one embodiment of a method of manufacture, a semiconductor is fabricated by immobilizing capture molecules on surfaces of electrical conductors. A solution is created that is used to form a gate region of the semiconductor. Electrodes are then deposited on opposing sides of the gate region. The resultant semiconductor can then operate as a transistor.

The apparatus and method provide several advantages. First, many (similar or different) biological semiconductors can be easily deposited on the same surface enabling simultaneous multi-sample (e.g., analyzing multiple patients for the same target) or multi-target (e.g., analyzing the same patient for multiple different targets) analysis on the same chip. The biological semiconductor does not require specialized fabrication facilities or experience, which lowers the overall cost and broadens the practical applications in which the semiconductors can be used. Furthermore, the semiconductor can be stored for long periods of time before use because of its stability. Finally, the semiconductor offers fast, continuous and nearly instantaneous detection of biological activity.

The foregoing and other objects, features, and advantages of the invention will become more apparent from the following detailed description, which proceeds with reference to the accompanying figures.

DETAILED DESCRIPTION

Terms and Techniques

Figures 1A, 1B:
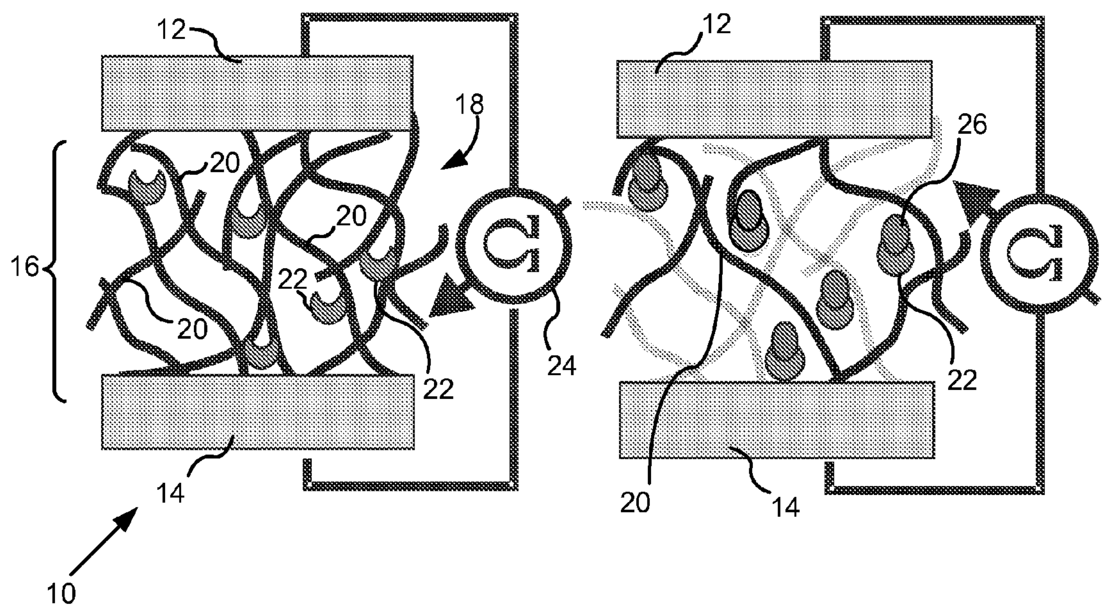
FIGS. 1A and 1B show schematic profile views of a semiconductor in a first state prior to injection of target biomolecules and a second state with captured target biomolecules disrupting conductivity of the semiconductor. The semiconductor includes a network of carbon nanotubes that form a three-dimensional matrix having width, depth, and length. Specific binding molecules are present on the nanotubes throughout the matrix (i.e., interior and exterior) for binding the target biomolecules. Although only two dimensions are shown in FIGS. 1A and 1B, it is understood that the network also extends perpendicular to the page. The disruption of the network is illustrated between FIG. 1A (prior to binding of the target) and FIG. 1B (after binding of the target) when the three-dimensional continuity of the network is disrupted to increase resistance.

Unless otherwise noted, technical terms are used according to conventional usage. Definitions of common terms in molecular biology may be found in *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided, along with the context of some of the terms in the present disclosure:

Analyte or Target:

an atom, molecule, group of molecules or compound of natural or synthetic origin (such as, but not limited to, a drug, hormone, enzyme, growth factor antigen, antibody, hapten, lectin, apoprotein, polypeptide, cofactor) sought to be detected or measured that is capable of binding specifically to at least one binding partner (such as, but not limited to, a drug, hormone, antigen, antibody, hapten, lectin, apoprotein, cofactor).

The analytes may include, but are not limited to, antigens from or antibodies to infectious agents (such as HIV, HTLV, *Helicobacter pylori*, hepatitis, measles, mumps, or rubella), drugs (such as cocaine, benzoylecgonine, benzodiazepine, tetrahydrocannabinol, nicotine, ethanol theophylline, phenytoin, acetaminophen, lithium, diazepam, nortriptyline, secobarbital, phenobarbitol, methamphetamine, theophylline, etc), hormones (such as testosterone, estradiol, estriol, 17-hydroxyprogesterone, progesterone, thyroxine, thyroid stimulating hormone (TSH), follicle stimulating hormone (FSH), luteinizing hormone (LH), transforming growth factor alpha, epidermal growth factor (EGF), insulin-like growth factor (ILGF) I and II, growth hormone release inhibiting factor, IGA and sex hormone binding globulin); and other analytes including antibiotics (such as penicillin), glucose, cholesterol, caffeine, cotinine, corticosteroid binding globulin, PSA, or DHEA binding glycoprotein.

Analytes vary in size. Merely by way of example, small molecule analytes can be, for instance, <0.1 nm (such as cotinine or penicillin, each with a molecular weight of less than about 1,000 Daltons). However, analytes may be larger, including for instance immunoglobulin analytes (such as IgG, which is about 8 nm in length and about 160,000 Daltons). Analytes can be polyvalent or monovalent. Examples of analytes are disclosed, for example, in U.S. Pat. No. 4,299,916; U.S. Pat. No. 4,275,149; U.S. Pat. No. 4,806,311; U.S. Pat. No. 6,001,558; and PCT Publication No. 98/39657.

A sample containing an analyte can be any biological fluid, such as, but not limited to, serum, blood, plasma, cerebral spinal fluid, sputum, urine, nasal secretions, sweat, saliva, pharyngeal exudates, bronchoalveolar lavage fluids, or vaginal secretions. Fluid homogenates can also be utilized as samples, such as cellular homogenates or fecal suspensions. Samples can also be non-biological fluids such as environmental samples, plant extracts, soil extracts or water samples. Typically a sample is in a liquid or an aqueous form, or may be an aqueous extract of a solid sample.

Antibody:

a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies can exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$ —$C_H$ 1 by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially an Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies. Embodiments of the assay that use antibodies can use any form of the antibodies, such as the intact immunoglobulin or fragments thereof that retain desired specific binding characteristics.

Antibodies can be monoclonal or polyclonal, but often will be monoclonal. Merely by way of example, such monoclonal antibodies can be prepared from murine hybridomas according to the classical method of Kohler and Milstein (*Nature* 256:495-497, 1975) or derivative methods thereof. Briefly, a mouse is repetitively inoculated with a few micrograms of the selected analyte compound (or a fragment thereof) over a period of a few weeks. In some instances, it will be beneficial to use an adjuvant or a carrier molecule to increase the immunogenicity and/or stability of the analyte in the animal system. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

Monoclonal antibodies to different analytes are commercially available. For instance, a monoclonal antibody to estriol-3 is produced by Fitzgerald Industries International (Concord, Mass.; Cat. #10-E37, Clone #M612039); likewise, Omega Biological, Inc. (Bozeman, Mont.) produces a monoclonal antibody to methamphetamine (Cat. #100-11-183, Clone Met 2). Rabbit anti-SEB can be purchased from Toxin Technology (Sarasota, Fla.).

Antigen:

a chemical or biochemical structure, determinant, antigen or portion thereof that is capable of inducing the formation of an antibody.

Avidin/Streptavidin:

The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NeutrAvidin Biotin Binding Protein (available from Pierce Biotechnology) with a mass of approximately 60,000 daltons.

The avidin-biotin complex is the strongest known non-covalent interaction ($Ka=10^{15}$ $M^{-1}$) between a protein and ligand. The bond formation between biotin and avidin is very rapid, and once formed, is unaffected by extremes of pH, temperature, organic solvents and other denaturing agents.

Although examples disclosed herein use streptavidin (SA) as a specific binding agent, the streptavidin could be substituted with other types of avidin. The term "avidin" is meant to refer to avidin, streptavidin and other forms of avidin that have similar biotin binding characteristics.

Binding Affinity:

a term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the invention that these constants be measured or determined. Rather, affinities as used herein to describe interactions between molecules of the described methods and devices are generally apparent affinities (unless otherwise specified) observed in empirical studies, which can be used to compare the relative strength with which one molecule (such as an antibody or other specific binding partner) will bind two other molecules (such as an analyte and an analyte-tracer conjugate). The concepts of binding affinity, association constant, and dissociation constant are well known.

Binding Domain:

the molecular structure associated with that portion of a receptor that binds ligand. More particularly, the binding domain may refer to a polypeptide, natural or synthetic, or nucleic acid encoding such a polypeptide, the amino acid sequence of which represents a specific (binding domain) region of a protein, which either alone or in combination with other domains, exhibits specific binding characteristics that are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited. The capture biomolecules disclosed herein may bind a binding domain of a target analyte.

Binding Partner:

any molecule or composition capable of recognizing and specifically binding to a defined structural aspect of another molecule or composition. Examples of such binding partners and corresponding molecule or composition include antigen/antibody, hapten/antibody, cellular receptor/ligand, lectin/ carbohydrate, apoprotein/cofactor and biotin/avidin (such as biotin/streptavidin). The term “specifically binds”, when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or vander Waals interactions, etc.

Biological Interaction:

A specific binding interaction that could or does occur in or with a living cell. For example, a biological interaction includes any interaction between binding pairs, such as protein binding (e.g., protein-protein binding or nucleic acid-protein binding), nucleic acid binding (e.g., protein-DNA, DNA-DNA, DNA-RNA, etc.), cellular receptor binding (e.g., a cell surface receptor or intracellular receptor that binds to a cellular ligand, such as a hormone).

Biotin Binding Protein:

A protein (such as a specific binding protein) that binds biotin with sufficiently great affinity for an intended purpose. Examples of biotin binding proteins are well known in the art, and include avidin, streptavidin, NeutrAvidin, and monoclonal antibodies or receptor molecules that specifically bind biotin.

Capture Biomolecule:

An organic molecule that is capable of production substantially by a living cell, and can specifically bind a target biomolecule by a biological interaction. Capture biomolecules can undergo non-cellular modifications (such as addition of functional groups) that cannot be added in a cell and still be considered a biomolecule. Example capture biomolecules include antibodies, nucleic acid molecules, aptamers, peptides and receptors. In particularly disclosed embodiments, the capture biomolecules may change conformation when binding to the target, and this change in conformation can disrupt the continuity of the network of nanotubes to result in increased resistance. This increase in resistance indicates the presence of the analyte, and the increase in resistance can in some embodiments be proportional to the amount (such as concentration) of target analyte present in the sample.

Carbon Nanotube:

As used herein, the terms “carbon nanotube” and the shorthand “nanotube” refer to carbon fullerene, a synthetic graphite, which typically has a molecular weight between about 840 and greater than 10 million grams/mole. The carbon nanotubes can be single-walled carbon nanotubes (SWCNT or SWNT) or multi-walled carbon nanotubes (MWCNT or MWNT). The present disclosure is not limited to any one method by which to produce carbon nanotubes. Rather, any suitable method can be used to produce carbon nanotubes for use in conjunction with methods and apparatus of this disclosure. Additionally, any size of carbon nanotube can be used. Carbon nanotubes suitable can have average diameters in the range of about 1 nanometer to about 25,000 nanometers (25 microns). Alternatively, the carbon nanotubes suitable can have average diameters in the range of about 1 nanometer to about 10,000 nanometers, or about 1 nanometer to about 5,000 nanometers, or about 3 nanometers to about 3,000 nanometers, or about 7 nanometers to about 1,000 nanometers, or even about 15 nanometers to about 200 nanometers. Alternatively, carbon nanotubes can have an average diameter of less than 25,000 nanometers, or less than 10,000 nanometers, or even less than 5,000 nanometers. Alternatively, carbon nanotubes suitable can have average diameters of less than 3,000 nanometers, or less than about 1,000 nanometers, or even less than about 500 nanometers.

The length of the carbon nanotubes is not critical and any length can be used. For example, carbon nanotubes can have lengths in the range of about 1 nanometer to about 25,000 nanometers (25 microns), or from about 1 nanometer to about 10,000 nanometers, or about 1 nanometer to about 5,000 nanometers, or about 3 nanometers to about 3,000 nanometers, or about 7 nanometers to about 1,000 nanometers, or even about 10 nanometers to about 500 nanometers. Alternatively, the carbon nanotubes can have a length of at least about 5 nanometers, at least about 10 nanometers, at least about 25 nanometers, at least about 50 nanometers, at least about 100 nanometers, at least about 250 nanometers, at least about 1,000 nanometers, at least about 2,500 nanometers, at least about 5,000 nanometers, at least about 7,500 nanometers, at least about 10,000 nanometers, or even at least about 25,000 nanometers. Still further, the carbon nanotubes can have lengths that would not be considered to be nano-scale lengths.

Still further, any kind of conductive nanowire can be used. Example nanowires include, but are not limited to metal nanowires, such as gold and silver or conductive polymers, such as polypyrolle, polythiophene, etc.

Detect or Determine an Analyte:

An analyte is “detected” when its presence is ascertained or discovered. “Determination” of an analyte refers to detecting an amount/concentration (either approximate or exact) of the analyte. Hence “detection” is a generic term that includes either ascertaining its presence or determining an amount/concentration (since determining an amount can also indicate the presence of the analyte). Embodiments of the device and method disclosed herein are capable of detecting the presence or determining a quantity of the analyte in a sample.

Electrical Conductors:

Electrical conductors are capable of allowing electrical charges, such as electrons, to move relatively freely along the conductor. Example electrical conductors include carbon nanotubes, graphene, and buckyballs.

Electrical Percolation:

Electrical percolation is used to characterize changes in the connectivity of elements within the network. Electrical percolation can be modeled as the flow of electricity through a randomly distributed network of conducting elements. In such a network, sites (vertices) or bonds (edges) are established by randomly placing resistors in a 3-D vector space with a statistically independent probability (p) of making contacts. At a critical threshold (pc), long-range connectivity within the vector space first appears (known as the “percolation threshold”). Beyond this threshold, the conducting elements increase precipitously and there is an onset of a sharp and very significant increase in the electrical conductivity of the material. Therefore, it is characteristic of the minimal concentration of conductive filler required to form a randomly distributed network that spans the whole material system. The concentration of conductive filler correlating to the percolation threshold will be affected, not by the mobility of electrons within the filler, but rather by the characteristics that control the number of contacts and the contact resistance between filler elements. Thus, the principles governing the percolation threshold are not “electrochemical”, but rather “electrophysical” (e.g., morphology, scale, and orientation of the filler).

Field-Effect Transistor (FET):

An FET is a type of transistor commonly used for weak-signal amplification (for example, for amplifying wireless signals). In the FET, current flows along a semiconductor path called the channel. At one end of the channel, there is an electrode called the source. At the other end of the channel, there is an electrode called the drain. The physical diameter of the channel is fixed, but its effective electrical diameter can be varied by the application of a voltage to a control electrode called the gate. The conductivity of the FET depends, at any given instant in time, on the electrical diameter of the channel. A small change in gate voltage can cause a large variation in the current from the source to the drain, which is how amplification of signals occurs. When nanowires are used to manufacture FETs, the nanowires must be positioned in a well-defined pattern and orientation, which requires specialized manufacturing techniques.

Immunogen:

a chemical or biochemical structure, determinant, antigen or portion thereof, that elicits an immune response, including, for example, polylysine, bovine serum albumin and keyhole limpet hemocyanin (KLH).

Matrix:

A three-dimensional region that contains the three-dimensional network of electrical conductors. The matrix can have a three-dimensional shape and can have an irregular structure. Capture biomolecules can be positioned throughout the matrix including on interior conductors and exterior conductors. In some embodiments, the capture biomolecules can be uniformly distributed throughout the width, length, and depth of the matrix.

Nucleic Acid:

A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Non-naturally occurring synthetic analogs include, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term “oligonucleotide” typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which “U” replaces “T.”

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the “coding strand;” sequences on the DNA strand having the same sequence as an mRNA transcribed from that DNA and which are located 5' to the 5'-end of the RNA transcript are referred to as “upstream sequences;” sequences on the DNA strand having the same sequence as the RNA and which are 3' to the 3' end of the coding RNA transcript are referred to as “downstream sequences.”

“cDNA” refers to a DNA that is complementary or identical to an mRNA, in either single stranded or double stranded form.

A first sequence is an “antisense” with respect to a second sequence if a polynucleotide whose sequence is the first sequence specifically hybridizes with a polynucleotide whose sequence is the second sequence. Hence, an antisense sequence can be used as a capture biomolecule to specifically bind a target nucleic acid molecule.

Terms used to describe sequence relationships between two or more nucleotide sequences or amino acid sequences include “reference sequence,” “selected from,” “comparison window,” “identical,” “percentage of sequence identity,” “substantially identical,” “complementary,” and “substantially complementary.”

Polypeptide:

A polymer in which the monomers are amino acid residues that are joined together through amide bonds, for example γ amide bonds (for example from the γ position of a glutamic acid side chain) or a amide bonds. When the amino acids are alpha-amino acids, either the L-optical isomer or the D-optical isomer can be used, for example D-glutamic acid to form poly-γ-D-glutamic acid (γDPGA). The terms “polypeptide” or “protein” as used herein is intended to encompass any amino acid sequence and include modified sequences such as glycoproteins. The term “polypeptide” is specifically intended to cover naturally occurring proteins, as well as those that are recombinantly or synthetically produced.

The term “polypeptide fragment” refers to a portion of a polypeptide which exhibits at least one useful epitope. The term “functional fragments of a polypeptide” refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

Sample or Specimen:

any cell, tissue, or fluid from a biological source (a “biological sample”), or any other medium, biological or non-biological, that can be evaluated in accordance with the invention, such as serum or water. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample of blood destined for a blood supply, a sample from a water supply, or the like. One example of a sample is a sample drawn from a human or animal to determine the presence or absence of a specific nucleic acid sequence.

A “sample suspected of containing” a particular component means a sample with respect to which the content of the component is unknown. For example, a fluid sample from a human suspected of having a disease, such as an infectious disease or a non-infectious disease, but not known to have the disease, defines a sample suspected of containing an infectious pathogen. Alternatively, the sample is one being analyzed for scientific research. “Sample” in this context includes naturally-occurring samples, such as physiological samples from humans or other animals, samples from food, livestock feed, etc. However, the sample can also be a product made in a research laboratory. Typical samples taken from humans or other animals include tissue biopsies, cells, whole blood, serum or other blood fractions, urine, ocular fluid, saliva, cerebro-spinal fluid, fluid or other samples from tonsils, lymph nodes, needle biopsies, etc. However, in particular examples disclosed herein, the samples are liquid samples.

Specific Binding Partner:

a member of a pair of molecules that interact by means of specific, non-covalent interactions that depend on the three-dimensional structures of the molecules involved. Exemplary pairs of specific binding partners include antigen/antibody, hapten/antibody, ligand/receptor, nucleic acid strand/complementary nucleic acid strand, substrate/enzyme, inhibitor/enzyme, carbohydrate/lectin, biotin/avidin (such as biotin/streptavidin). Examples include a hormone binding to receptors, and virus/cellular receptor. The methods and devices disclosed herein can be used for any analyte for which a specific binding partner exists.

The phrase "specifically binds to an analyte" (or "specifically immunoreactive with" when referring to the particulars example of an antibody) refers to a binding reaction which is determinative of the presence of the analyte in the presence of a heterogeneous population of molecules such as proteins and other biologic molecules. A cellular receptor is, for example, capable of specifically binding to an analyte. In immunoassay conditions, the specified antibodies bind to a particular analyte and do not bind in a significant amount to other analytes present in the sample. A variety of immunoassay formats may be used to select antibodies specifically immunoreactive with a particular analyte. For example, solid-phase ELISA immunoassays are routinely used to select monoclonal antibodies specifically immunoreactive with a protein. See Harlow and Lane, *Antibodies, A Laboratory Manual*, CSHP, New York (1988), for a description of immunoassay formats and conditions that can be used to determine specific immunoreactivity.

Target Analyte:

An analyte to be detected by the detector, and which binds to the specific binding partner on the nanotube.

Three-Dimensional Network:

A complex, interconnected group of electrical conductors allowing electrical charge to pass between two points using multiple and unique electrical paths. For example, the network is an unpatterned, random interconnection of electrical conductors. If any electrical paths in the network are disrupted, electrical charge can still pass between the two points using alternative electrical paths in the network. The three-dimensional network can be any size (i.e., any length, depth, and width), depending on the application. One example can use carbon nanotubes of at least 0.4 nm in diameter. The desired depth and width of the network can be greater than a single nanotube, such as 2, 3, 4, 5, etc. times the thickness of a single nanotube. Other thicknesses can be between 10 to 100 times the thickness of a single nanotube.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." It is further to be understood that all molecular weight or molecular mass values are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

The disclosure is illustrated by the following non-limiting Examples.

FIG. 1A shows a biological semiconductor 10 having opposing electrodes 12, 14 with a gate region 16 positioned there between. The gate region 16 includes a matrix 18 of electrical conductors 20 that create a plurality of electrical connections between the electrodes 12, 14. The electrical conductors form a three-dimensional network of individual entangled or overlapping conductors. A plurality of capture biomolecules 22 are shown as half-moon shapes and are positioned within the matrix 18. The capture biomolecules 22 are shown connected to the exterior surface of the carbon nanotubes, but are contained substantially within the interior region of the matrix of entangled conductors. The matrix 18 is a multi-layer, three-dimensional network that can be made of a variety of conductive materials, such as carbon nanotubes (e.g., single-walled carbon nanotubes), graphene, buckyballs, or other fullerene material. Other materials can also be used, such as metal nanowires, made of gold, silver, etc. or conductive polymers, such as polypyrolle, polythiophene, etc. By multi-layered, it is meant that multiple of the electrical conductors 20 are interconnected in the network in three-dimensional space. The matrix 18 can be a solid or a solution, depending on the application. The electrodes 12 are made of a conductive metal, such as silver, but other conductive metals can be used. The capture biomolecules 22 are capable of binding/interacting with target molecules, such as antibodies, nucleic acid molecules, aptamers, peptides, etc. The electrical conductors 20 are bound in a way as to not overly confine the conductors to allow movement in response to biomolecular binding between the capture biomolecules and targets, which are introduced into the gate region 16. Although not shown, the gate region 16 can be protected or shielded from the outside environment using a polymer-based coating or layer, such as of polydiallyldimethylammonium chloride or other suitable covering material. Such a covering material limits any surface interaction occurring in the gate region 16, which could impact results. The specimen can interact with the gate region by adding the specimen prior to placing a covering material or by placing the gate in a flow cell and injecting the specimen in the flow cell.

The opposing electrodes 12, 14 are electrically coupled to a resistance measuring device 24 for reading a resistance of the biological semiconductor across the gate region 16. For example, the resistance measuring device can be a commercially available ohm meter.

The concentration of conductive material in the matrix 18 is such that the material is at or near a percolation threshold. The conductivity of the semiconductor 10 depends on the number of contacts in the network between the electrical conductors 20. This number of contacts can be varied through molecular interactions, which changes the spacing orientation, and continuity of the matrix 18. The binding of target analyte to the receptors within the matrix disrupts the pre-binding architecture of the matrix to change the conductivity of the matrix. As a result, the molecular interactions also change the resistance of the matrix 18, which can be used to indicate the presence and/or number of molecular interactions. A quantitative change in resistance can be made to correlate with a particular quantity (such as a concentration of the target molecule).

FIG. 1B shows target molecules 26 bound to the capture biomolecules 22. As can be seen, the molecular interactions between the capture biomolecules and the target molecules disrupt the matrix continuity resulting in increased resistance. The molecular interaction can include binding of antigens to antibodies, nucleic acid binding, hormone binding to a receptor, etc. Because the conductors 20 are not overly confined to allow for movement, some electrical paths between the electrodes 12, 14 break, which forces current to pass through other conductors, increasing overall resistance. Thus, FIG. 1A represents a low-resistance mode of operation. In a particular example, single-walled nanotubes were used (shown in black lines) with no antigens bound to antibodies (shown as half-moon shapes). By contrast, FIG. 1B represents a high-resistance mode wherein binding of antigens (ovals) results in disruption of the three-dimensional matrix (non-contact SWNTs are shown in grey) thus increasing electrical resistance. Disruption of the three-dimensional matrix means that some of the conductive paths between electrodes have been severed, while other conductive paths remain intact.

FIGS. 1A and 1B, therefore, show that the semiconductor is based on electrical percolation, rather than FETs where channel width changes as a result of gate activity. Semiconductors based on electrical percolation are easier to manufacture than FETs, as there is no need for direct chemical vapor deposition or specialized expertise needed for FET manufacture. FETs require specific patterned, structured placement of nanowires. By contrast, semiconductors formed using the techniques described herein use an unoriented, unstructured, pattern less, mesh-like network of interconnected conductors. The binding molecules are therefore distributed throughout the interior of the gate region, instead of being confined to an outer surface. Unlike FET's, various binding partners can be used to functionalize pre-made SWNT gates in bulk. The gates can then be simply printed or deposited onto non-conductive materials.

Figure 2:
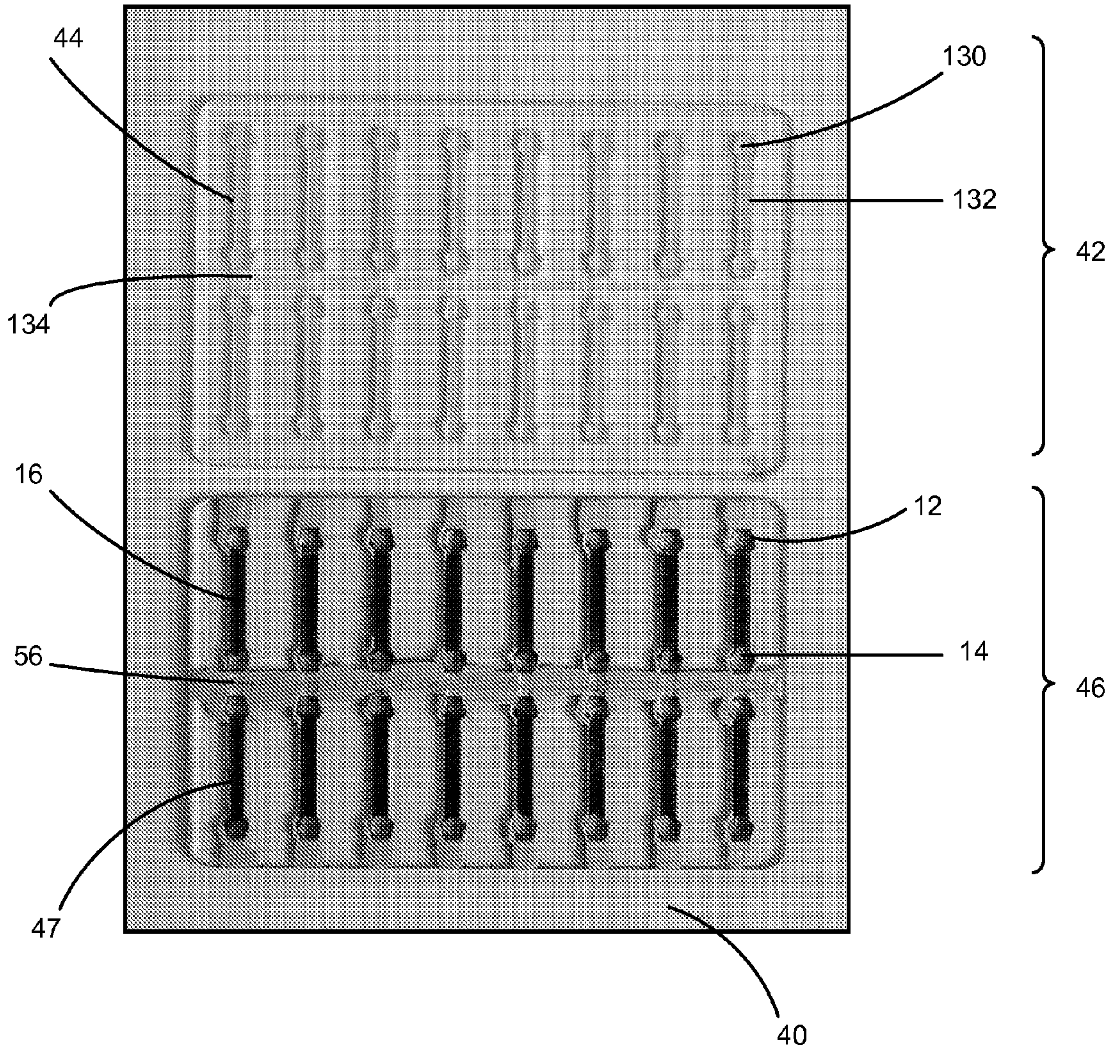
FIG. 2 shows an exemplary mold having a blank top portion and a bottom portion with a circuit including sixteen semiconductors fabricated in parallel.

FIG. 2 shows a tray 40 that can be used to assemble a plurality of biological semiconductors in parallel. The tray acts as a base substrate and can be made of plastic or other non-conductive material. An upper portion 42 of the tray is blank and has a plurality of blank forms 44 for making biological semiconductors. The forms can be any shape and dimensions. A lower portion 46 has sixteen biological semiconductors coupled in parallel, such as a biological semiconductor shown at 47. Although sixteen are shown, the number of biological semiconductors can be any desired number simply by modifying the size of the tray 40. Alternatively, the biological semiconductor can be manufactured as a stand-alone device, such as a more traditional transistor package or chip. Positive electrodes 12 are floating and are used to connect a positive lead of an ohm meter or other resistance measuring device. Negative electrodes 14 are coupled together through an electrical common 56 that extends the width of the tray. Any number of the electrodes 50 can be coupled to one or more resistance measuring devices. Between the positive and negative electrodes 12, 14 are the gate regions 16 having a three-dimensional network into which one or more different specimens may be injected. Upon injection, molecules of the specimen can bind with capture biomolecules in the network resulting in increased resistance across a gate region of the biological semiconductor. Some of the biological semiconductors in the tray 40 can act as control elements, which are used as a baseline to show the resistance of the biological semiconductors without any molecular reactions. Such a baseline is needed in order to determine a difference between a measurement of resistivity of a biological semiconductor that had a detectable target molecule and a biological semiconductor that had no specimen introduced or that had limited or no molecular binding. One example of how to use the biological semiconductors is that each biological semiconductor can have a different antibody associated with it. A user's sample can be injected into all sixteen gate regions and sixteen different readings can be taken to determine different antigens in the sample.

In the particular example of FIG. 2, the gate regions 16 are circular in cross section (i.e., cylindrical in three-dimensions), but other shapes can be used, such as rectangular, square, etc.

Figure 3:
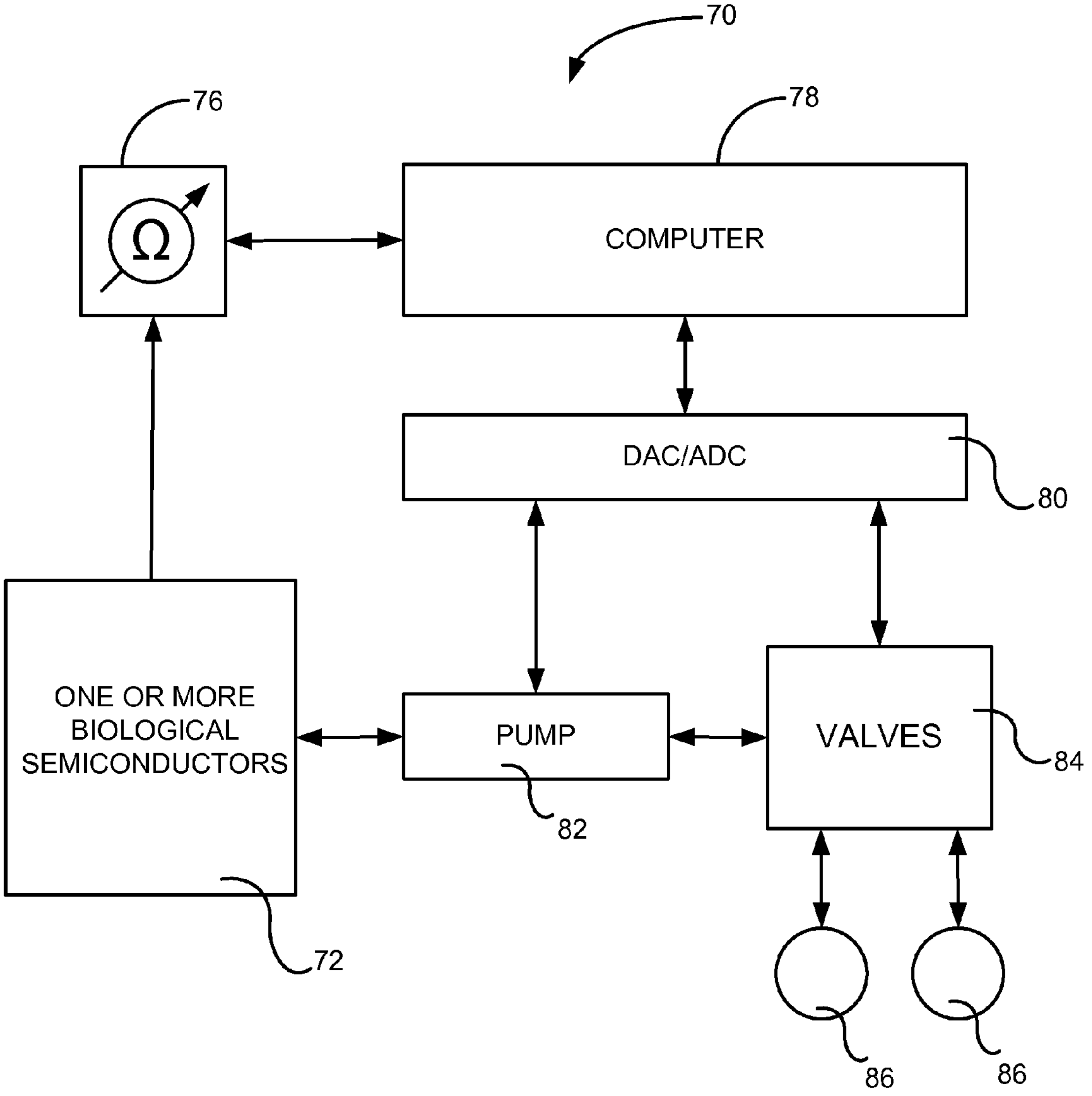
FIG. 3 shows a system for continuous monitoring of a circuit including or more biological semiconductor.

FIG. 3 shows a system 70 for implementing continuous monitoring. One or more biological semiconductors 72 include networks with capture biomolecules to which targets are bound. An electrical resistance detector 76 continuously monitors one or more of the biological semiconductors in order to detect molecular interactions. The resistance detector can be an ohm meter or other devices for measuring current, voltage, resistance capacitance or impedance. The detector 76 is coupled to a computer 78 that monitors and stores readings from the detector. Periodic readings can be taken and compared to control readings where no biomolecular activity occurred. The computer 78 can be coupled to a digital-to-analog converter 80, which allows the computer 78 to communicate with a pump 82 and a plurality of valves 84. The valves 84 can be coupled to one or more specimens 86, which are samples to be injected into the biosemiconductors in order to detect biomolecules therein. If two-way communication is desired between the computer 78 and the pump and valves, an analog-to-digital converter can be housed together with the digital-to-analog converter, as is shown at 80. Such two-way communication may be desirable to monitor that state of the valves and the pumping mechanism. In general operation, the computer releases one or more of the specimens 86 by controlling the valves 84. The pump 82 then pumps the specimen released by the valves and injects it into the gate region 16 of the semiconductor for analysis. Using the system 70, biomolecular sampling and detection can be fully automated.

Figure 4:
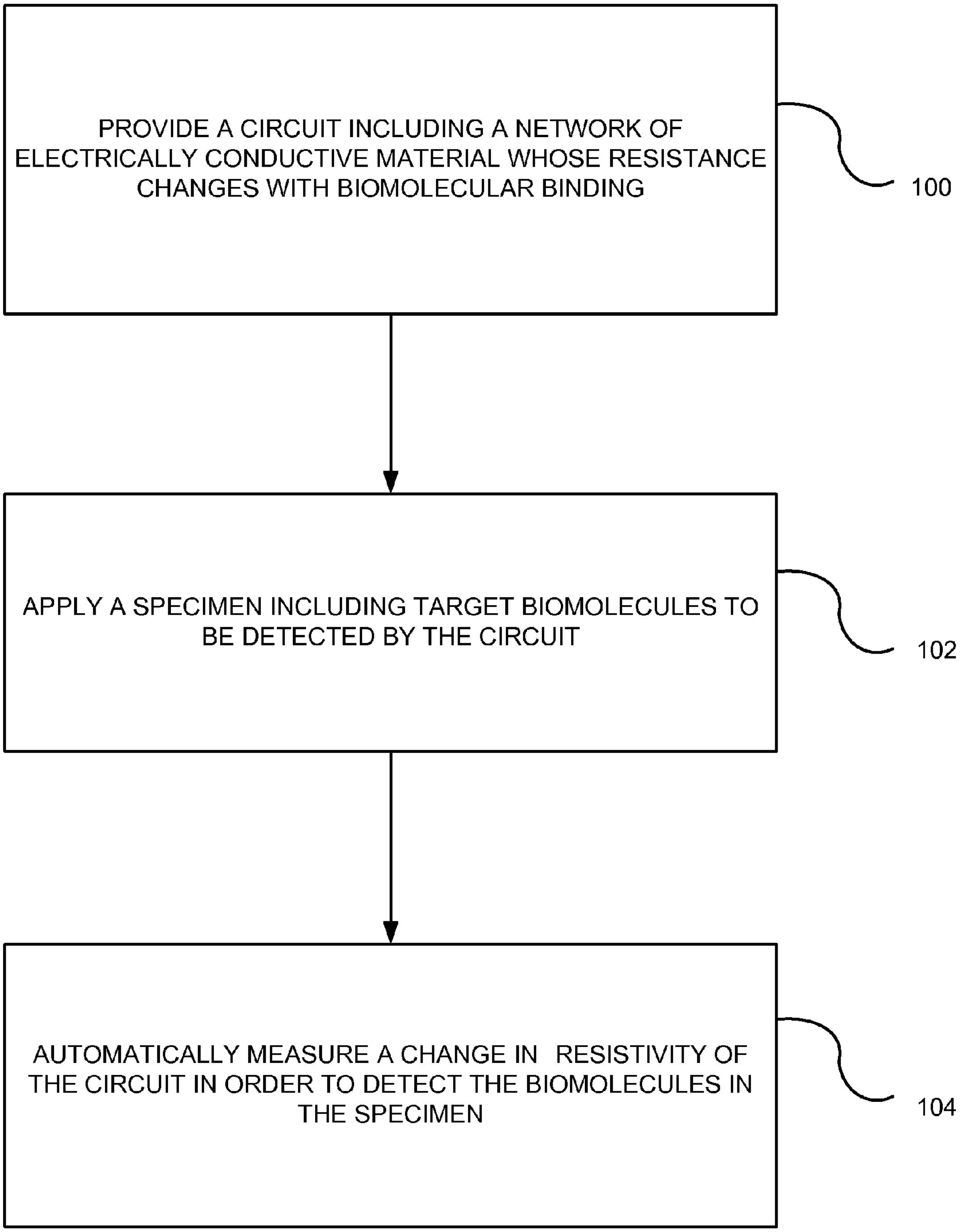
FIG. 4 is a flowchart of a method for detecting biomolecular interactions in the semiconductor.

FIG. 4 is a flowchart of a method for detecting and measuring biomolecules in a specimen. In process block 100, a circuit is provided including a biosemiconductor with a gate region of electrically conductive material whose resistance changes with biomolecular binding. An example semiconductor is shown in FIG. 1 and example circuits are shown in FIGS. 1, 2 and 3. In process block 102, a specimen is applied to the circuit including target biomolecules to be detected by the circuit. For example, automatic application can occur using the system of FIG. 3. Alternatively, manual application can be used. In process block 104, automatic measurement of resistivity can be performed, such as using resistance detector 76 of FIG. 3. Using the measured resistance, a change is resistivity as compared to a previous measurement can be performed.

Figure 5:
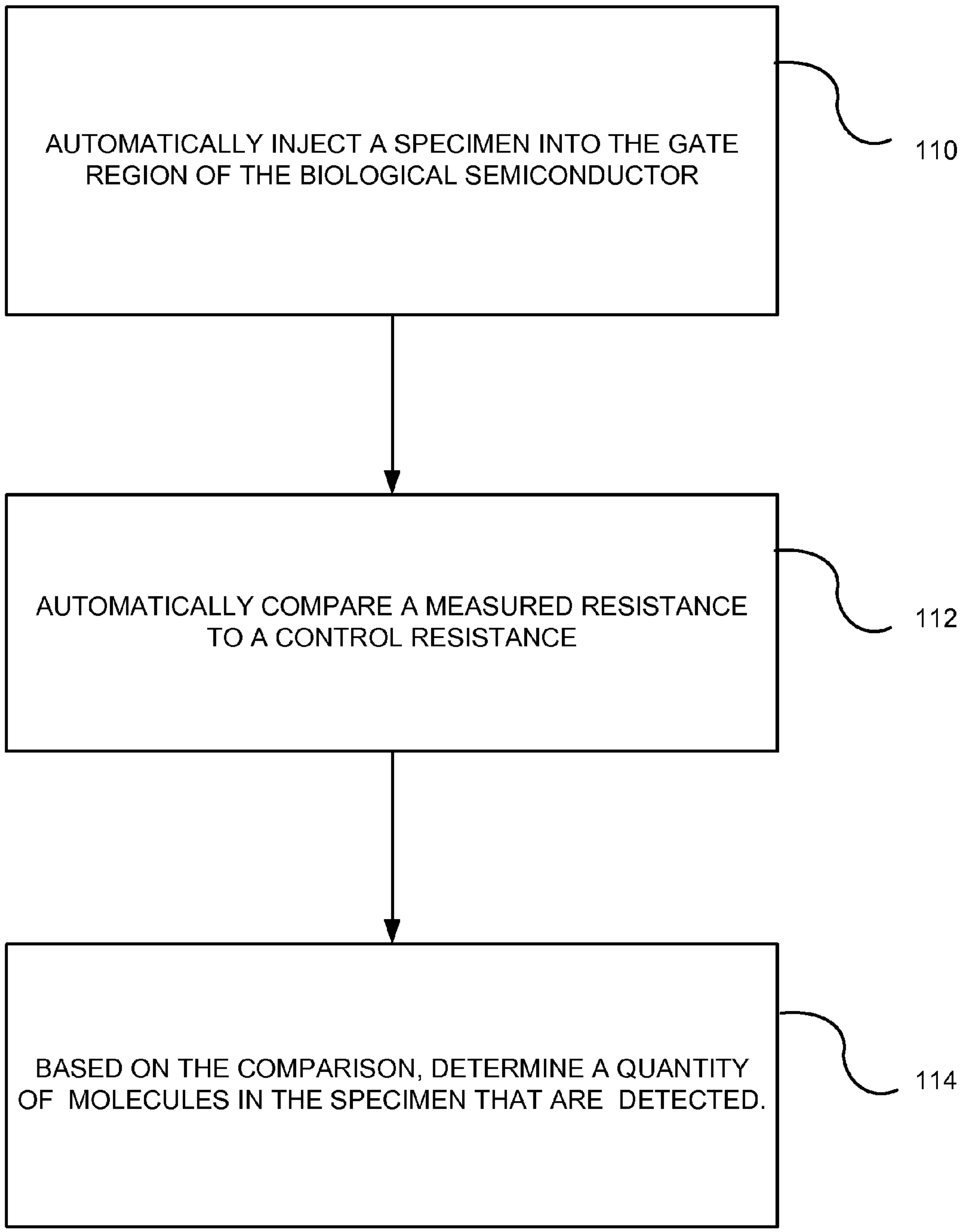
FIG. 5 illustrates additional process features that can be performed.

FIG. 5 shows a flowchart of a method showing additional processes that can be performed in conjunction with the processes of FIG. 4. In process block 110, the specimen can be automatically injected into the gate region 16 of the semiconductor. Such automatic injection can occur through using a pump 82 (FIG. 3), which is responsive to a computer 78, for pumping the specimen released by control valves 84 and delivering the specimen to the gate region 16 of a semiconductor. In process block 112, an automatic comparison is made between the measured resistance and a control resistance. Such automatic comparison can occur using the computer 78. For example, the computer 78 can measure a control resistance obtained through measuring the resistance of a biological semiconductor that does not have molecular binding pairs as described above. In process block 114, using a difference calculation between the measured resistance and a control resistance, a quantity of biomolecules in the specimen can be determined.

Figure 6:
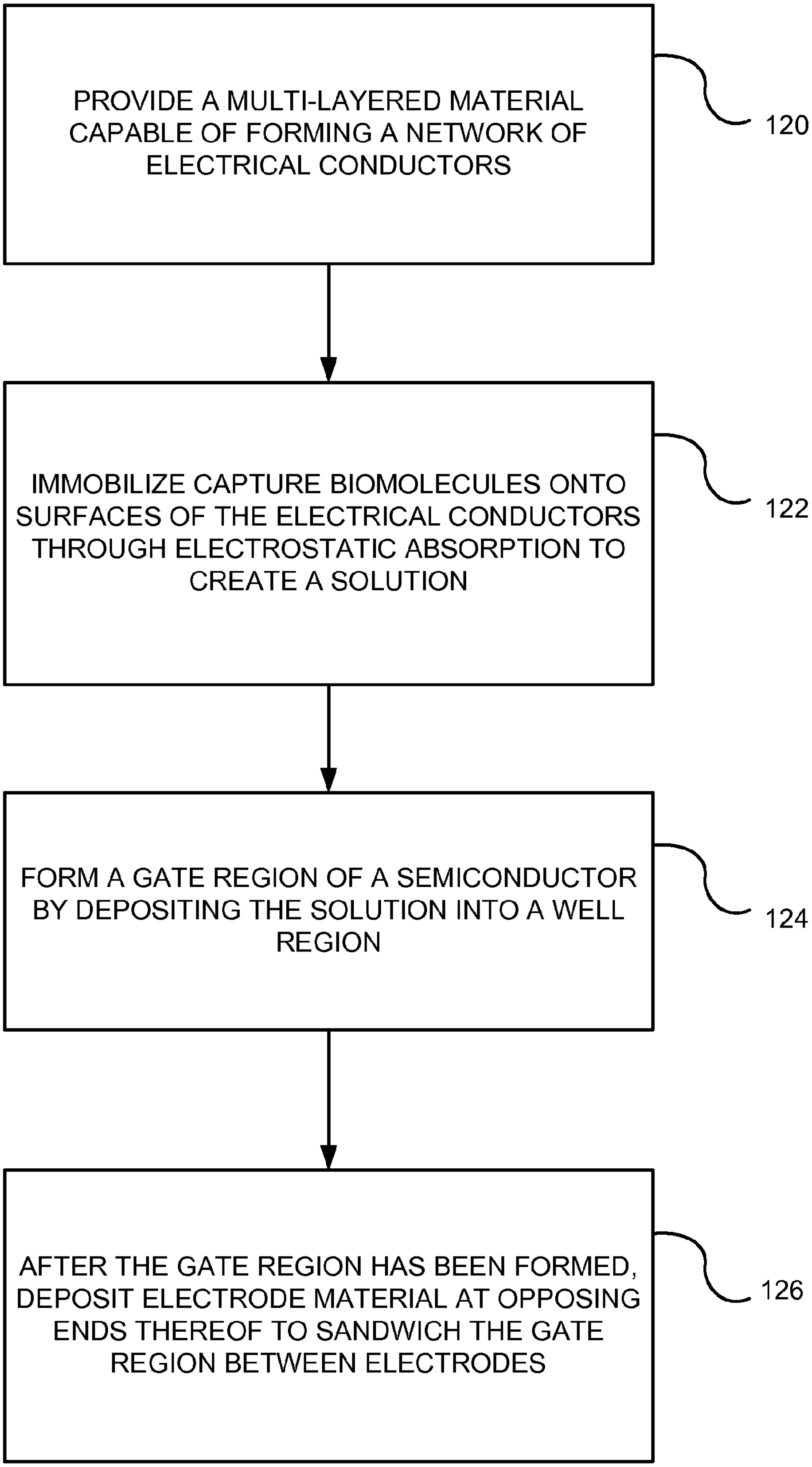
FIG. 6 is a flowchart of a method for fabricating the semiconductor of FIG. 1.
Figure 11A:
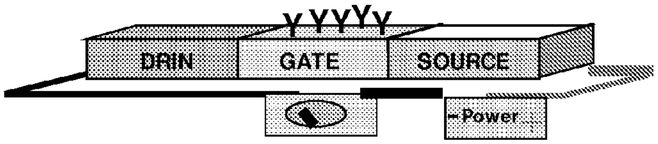
FIGS. 11A-C show a transistor made according to another example without electrodes on the chip.

FIG. 6 is a method of manufacturing a semiconductor for measuring biological interactions. In process block 120, a multi-layered material is provided that is capable of forming a network of electrical conductors. The multi-layered material can be formed from a bio-nanocarbon material, such as carbon nanotubes (e.g., single-walled carbon nanotubes), graphene, buckyballs, etc. In process block 122, capture biomolecules are immobilized onto surfaces of electrical conductors in the bio-nanocarbon material through electrostatic absorption, using techniques well known in the art. An example of how to attach biomolecules onto bio-nanocarbon material is described in the following article: Yang, M; Kostov, Y; Bruck, H; and Rasooly, A, "Carbon Nanotubes with Enhanced Chemiluminescence Immunoassay for CCD-Based Detection of Staphylococcal Enterotioxin B in Food," Analytical Chemistry, Vol. 80, No. 22, Nov. 15, 2008, which is hereby incorporated by reference. Typically, the resultant multi-layered material is in solution form. In process block 124, a gate region of a semiconductor is formed by depositing the solution into a well region of a transistor. An example well region is shown in FIG. 2 at the center of blank form 44. The result is the gate region 16 is formed that is a three-dimensional network of electrical conductors. In process block 126, after the gate region has been formed, electrode material (e.g., silver, gold, etc.) is deposited at opposite ends of the gate region to create a semiconductor, such as a transistor. Alternatively, no specific electrodes are needed and the leads of the measuring device can be connected directly to opposing ends of the gates (See FIG. 11). A specific example of manufacture for the gate region is provided below. Additional techniques are well known in the art. Suitable densities of nanotube material can be derived from percolation curves associated with the material used. For example, in FIG. 8A, the density determined can be based on where the percolation curve levels off, such as between 0.5 and 1.5. Some examples densities have been shown in the art and are described in U.S. Pat. No. 6,918,284, at column 2, lines 54-64, which is hereby incorporated by reference.

Figure 7:
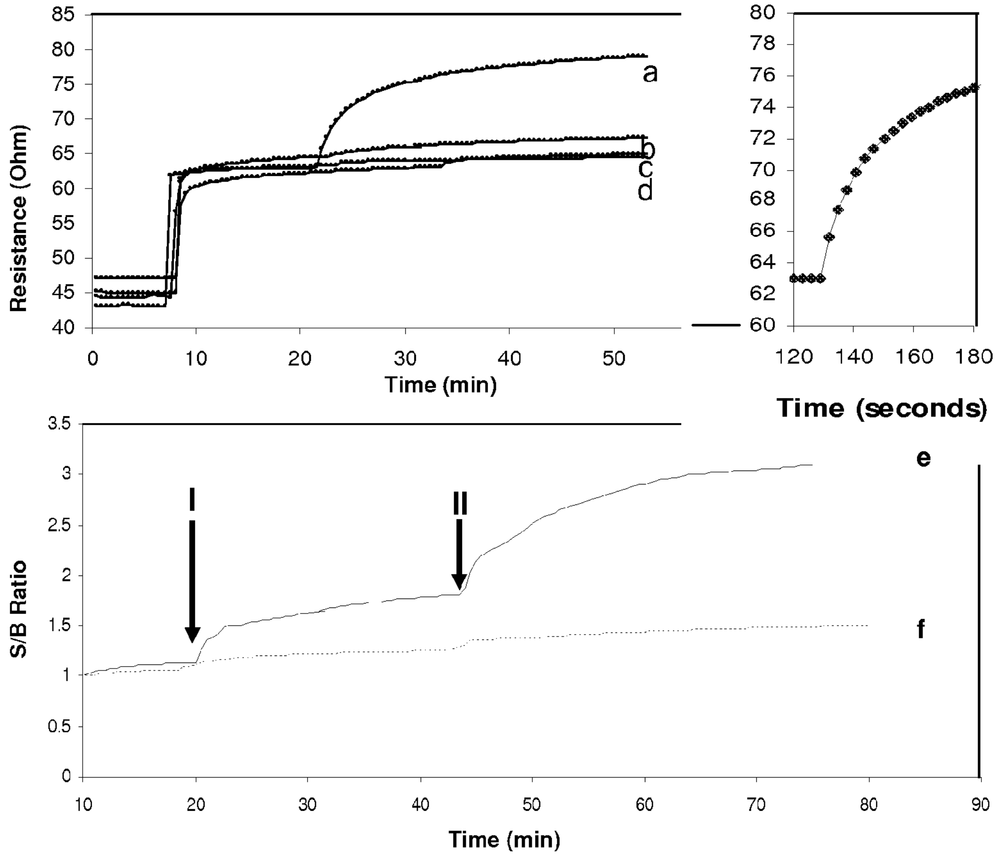
FIG. 7 shows data from example injections of target biomolecules into a plurality of biological semiconductors, illustrating changes in resistance of the network.

FIG. 7 includes graphs A, B, and C showing an experiment with the system in continuous monitoring mode. Staphylococcal enterotoxin B (SEB) was injected into the biological semiconductors. Different controls were used for nonspecific binding. The trace labeled "a" shows 100 ng/mL of SEB. As can be seen, all traces react nearly simultaneously to injection of target biomolecules. The trace labeled "b" shows 1 g/mL BSA. The trace labeled "c" shows 1 g/mL of lysozyme. And the trace labeled "d" shows 1 g/mL IgG applied to a sensor. Graph B demonstrates the rapid response of the biological semiconductor. Graph C demonstrates SEB is bound to the biological semiconductor by having a first injection of SEB, shown at I, and a second injection shown at II. The signal is detected as shown by trace "e", but it is not detected in control trace "f."

Example 1

Using Single-Walled Carbon Nanotubes

A detector was fabricated with the bio-nanocomposite material by depositing pre-functionalized single-walled nanotubess (SWNTs) with biological ligands to form a biological semiconductor (BSC) layer.

A simplified prototype of the BSC sensor is shown in FIG. 2. The BSC is a unipolar device, with two electrodes painted with silver contact paste on both sides of the printed SWNT-antibody bio-nanocomposite. Several BSCs can be easily fabricated in a row on the same surface. At the circuit level, each BSC contains a connection well, shown at 130 for the silver electrode, a channel, shown at 132 for the bio-nanocomposite and a channel 134 for the silver electrode that functions as a common ground point for all BSCs. The resultant plurality of semiconductors are shown in the lower portion 46 of FIG. 2.

The SWNTs were functionalized with rabbit anti-SEB IgG. A previously developed CNT functionalization scheme is employed for binding the SWNTs with antibodies. The fabrication and preparation of the carbon nanotubes is described in more detail in Example 2. The bio-nanocomposite is then immobilized by drying it directly on the surface of either Poly(methyl methacrylate) (PMMA) or polycarbonate wells fabricated by laser micromachining.

The BSC is operated simply by measuring the electrical resistance between the silver paste electrodes. Binding of the specific antigen to the antibody disrupts the network and increases the resistance. The amount of binding of the specific antigen to the antibody controls the overall resistance of the electrical percolation BSC network, which is measured by an ohmmeter via each BSC electrode 50 and the common electrode 56.

A circuit board with sixteen electrical percolation BSCs was used in a conventional immunodetection assay by allowing binding of SEB to the antibody gate and washing off unbound material. The measurement value was calculated as the difference between the initial reading recorded (R0) with no SEB and the reading with SEB (R1). The difference between the two readings (R1−R0) was measured as the signal, and is normalized by R0 to obtain the signal-to-baseline ratio. FIG. 8 includes two graphs showing concentration levels for single-walled carbon nanotubes. Varying concentration levels can be used based on the application, but for single-walled carbon nanotubes it is believed that a concentration of about between 1 and 1.5 mg/ml is suitable. Whatever material is used, the concentration levels can be chosen to that the network is maintained at around the percolation threshold so that any molecular interactions can have a measurable impact on resistance. Using percolation principles, it is possible to characterize changes in the connectivity of elements within the network by modeling electrical percolation as the flow of electricity through a randomly distributed network of conducting elements. In such a network, sites (vertices) or bonds (edges) are established by randomly placing resistors in a 3-D vector space with a statistically independent probability (p) of making contacts. At a critical threshold (pc), long-range connectivity within the vector space first appears (known as the "percolation threshold"). Beyond this threshold, the conducting elements increase precipitously and there is an onset of a sharp and very significant increase in the electrical conductivity of the material. Therefore, it is characteristic of the minimal concentration of conductive filler required to form a randomly distributed network that spans the whole material system. The concentration of conductive filler correlating to the percolation threshold will be affected, not by the mobility of electrons within the filler, but rather by the characteristics that control the number of contacts and the contact resistance between filler elements. Thus, the principles governing the percolation threshold are not "electrochemical", but rather "electrophysical" (e.g., morphology, scale, and orientation of the filler).

Figure 8A:
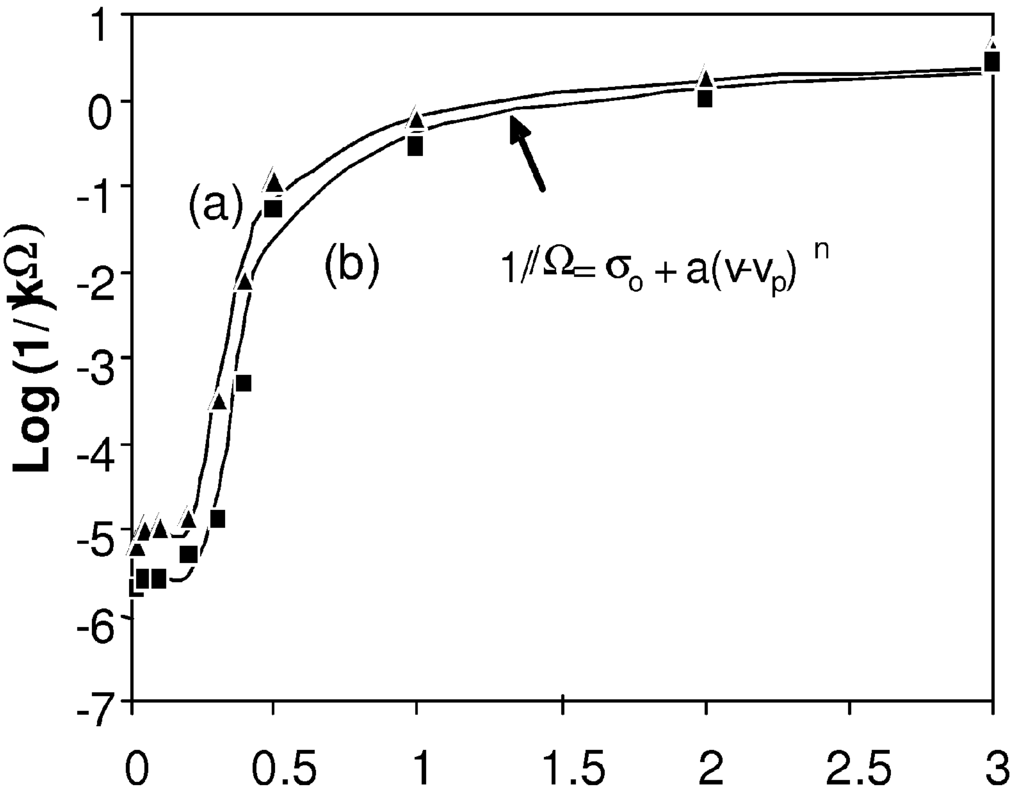
FIGS. 8A and 8B illustrate percolation curves of a single-walled carbon nanotube and signal-to-baseline levels versus concentration levels of single-walled carbon nanotubes according to a first example.

FIG. 8 shows an establishment of a percolation threshold of the SWNT-antibody network using various concentrations of SWNT immobilized onto a PMMA surface without (FIG. 8A, labeled (a)) and with anti-SEB antibody (FIG. 8A, labeled (b)). Their resistance was measured to determine the percolation threshold, vp, using a conventional power law equation from percolation theory with a baseline resistance. Using a power law fit, it was possible to determine that the percolation threshold for the SWNT-antibody network is between 0.2 to 0.3 mg/mL, and does not change significantly after antibody immobilization. The rate of change in resistance is directly related to the power-law exponent, n, which was 8 and the power-law coefficient, a, which was 5.×10−6, in this particular example. There are three characteristic regimes in SWNT concentration associated with these values: (1) between ~0.2 to 0.5 mg/mL the percolation threshold is characterized by a steep change (approximately four orders of magnitude) in resistance due to the onset of percolation, (2) between ~0.5 to 1 mg/mL the change levels off and the increase is approximately one order of magnitude, (3) over ~1 mg/ml the resistance levels off and does not change significantly with higher concentrations of SWNT resulting in complete percolation. Over the entire range, the total change in resistance is approximately five orders of magnitude. The percolation threshold of the SWNT-antibody bio-nanocomposite network also indicates that its typical resistance (FIG. 8A, labeled (b)) will be higher than the resistance that is attributed to the SWNT only (FIG. 8A, labeled (a)), presumably due to the contacts between the antibody and the functionalized SWNT.

At the percolation transition point, the point above the percolation threshold where the change in resistance begins to level off, there is a still relatively low statistical distribution of "contacts" between the CNT-antibody complexes in the network. Therefore, small changes in the CNT-antibody complexes can lead to dramatic changes in conductivity. Based on this model, the bio-nanocomposite prepared with 1 mg/mL of SWNT will be the most sensitive to molecular interactions for immunodetection, since this is the concentration at which the change in resistance begins to level off, consistent with the complete percolation of the SWNTs.

Figure 8B:
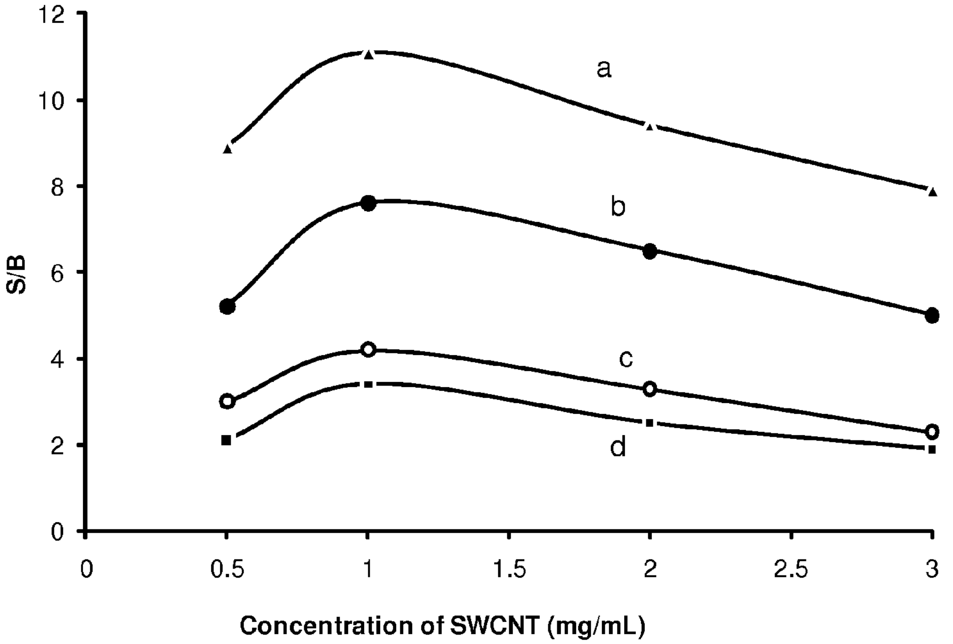

To validate the prediction that the point where complete percolation occurs (1 mg/mL) will be the most sensitive to molecular interactions, the response of the BSC over a range of SWNTs concentrations (0.5-3 mg/ml) was analyzed in response to binding of broad range of SEB concentration (0.5-100 ng/ml). At the transition point of 1 mg/ml, the BSC exhibited peak sensitivity to all SEB concentrations (FIG. 8B). This result suggests that the mechanism of the BSC sensor is electrical percolation. Moreover, for all concentrations of SWNTs bio-nanocomposite, the S/B increases with increasing SEB concentration, suggesting that the new BSC can be used for direct biosensing and bioactuation.

Figure 9:
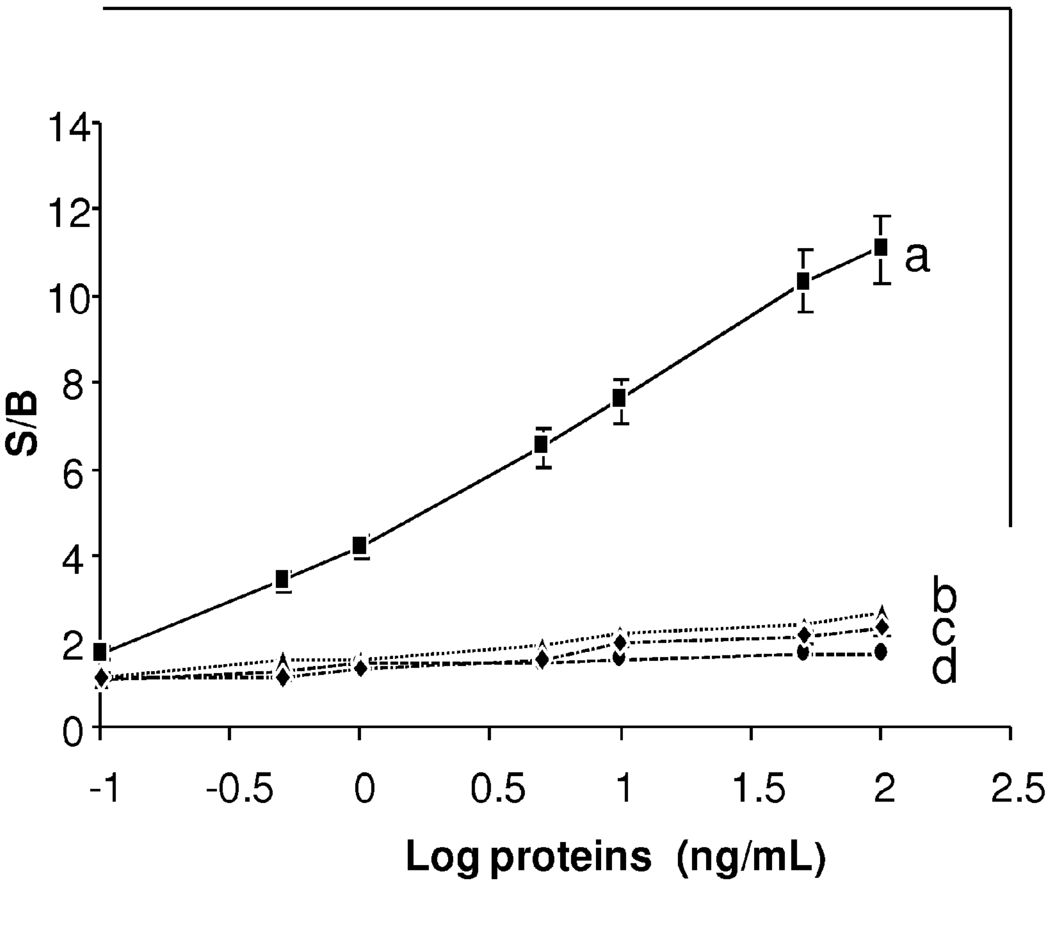
FIG. 9 shows signal-to-baseline levels versus measured proteins, according to the first example.

To show the specificity of the BSC response, various amounts of SEB (from 0.1-100 ng/mL) in buffer were added to the chip with 1 mg/ml of SWNT (FIG. 9, labeled (a)). The resistance increased proportionally to the amount of SEB. Non-specific antigens were used to study the BSC leak rate, which is the change in resistance with non-specific binding and is an indication of the specificity and the selectivity of BSC actuation. Various non-specific antigens were used, including a smaller molecular weight (14 kDa) protein, lysozyme (FIG. 9, labeled (b)), and a higher molecular weight (150 kDa) protein, human IgG (FIG. 9, labeled (c)). As shown in FIG. 9, the level of non-specific binding in these semiconductors is relatively small regardless of concentration, which is similar to the S/B for SEB concentrations when there is no antibody on the SWNTs (FIG. 9, labeled (d)).

To determine the limit of detection (LOD) for SEB, the S/B ratio from eight replicas of various concentrations of SEB was compared to buffer. A T-test demonstrated that at 1 ng/ml, the S/B ratio is significantly different ($P<0.00017$) from the value using buffer only. Thus, the current configuration has a LOD of 1 ng/mL for SEB.

Figure 10:
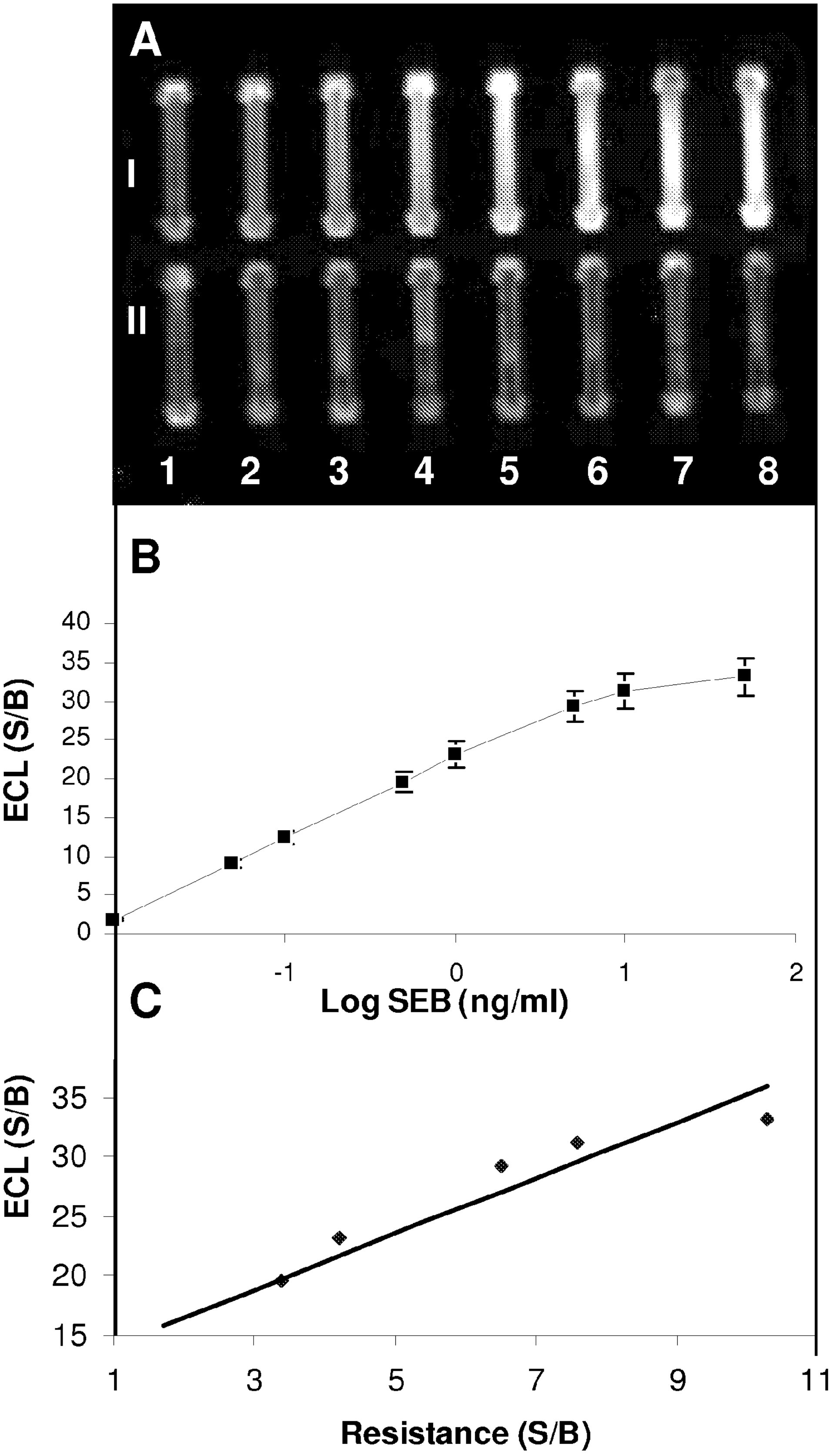
FIG. 10 is an illustration showing that quantitative measurements in FIG. 9 correspond to traditional quantitative measurement methods using labeling and optical sensing, according to the first example.

To confirm that the percolation of the SWNT-antibody and the antibody gate mechanisms depend on SEB binding, an independent measurement of bound SEB to the SWNTs bio-nanocomposite was carried out using a sandwich immunoassay detected by Enhanced Chemiluminescence (ECL). As shown in FIG. 10A, the intensity of the signal from the captured SEB on the BSC chip is proportional to the amount of SEB. Quantitative analysis of the data (FIG. 10C) suggests a high correlation between the amount of SEB and the ECL signal and that there is a very high correlation (R2=0.9942) between the electrical measurements (FIG. 9) and the ECL measurements (FIG. 10B). The linear regression is also highly significant ($p<0.0056$), suggesting that the anti-SEB antibody on the BSC chip did indeed capture SEB, and that the direct electrical measurements are in agreement with the indirect sandwich immunoassay detected by ECL.

The data suggests that antigen binding leads to rearrangement of the SWNT-antibody network, resulting in physical depletion of electron carriers in the bulk of the SWNT-antibody bio-nanocomposite through changes in contact between the SWNTs. Such contacts are analogous to the physical edge of the conduction band. At this point, the antibody gate mechanism initiated by binding the antigen to the antibody shifts the complex closer to the band gap, which is an energy range where statistically few electron states exist so fewer electrons can jump between SWNTs. This is analogous to decreasing an electric field in a classical semiconductor, and therefore increases the electrical resistance of the SWNT-antibody network. The percolated SWNT-antibody network can therefore be considered the "conduction band", and the number of electrons in the conduction band (i.e., the band gap) is physically determined by the number of SWNT-antibody complexes in the conduction band, rather than by the conventional electronic band gap at the surface of the SWNT that is responsible for electrochemical detection principles.

Unlike field-effect transistors (FETs) based sensors, which rely on an electric field at the surface of the SWNTs to control conductivity, the response of the electrical percolation BSC can be attributed to the number of contacts of carbon nanotubes within the network. Since the number of contacts can be varied by molecular interactions (i.e., by antibody-antigen binding), changes in the resistance of the network can be used to determine the number of interactions and hence the concentration of the target molecule.

One attractive feature of electrical percolation BSCs based on SWNTs is the simplicity of the preparation (screen printing). In contrast, FETs are often fabricated using chemical vapor deposition (CVD) and require a high-tech infrastructure for microfabrication of solid-state semiconductor components. Furthermore, unlike FETs which are constructed with SWNTs as a single wire or sub-monolayer network, BSC do not need to be oriented. In fact, a multi-layer mesh-like network is preferred. Electrical percolation BSCs can simply be printed on any non-conductive material to create biosensors capable of detecting a variety of molecules. Selectivity is achieved by printing different specific biological "gates", such as antibodies, DNA, receptors, or aptamers, taking advantage of the natural selectivity of these biological molecules. Moreover, electrical percolation BSC production can be readily scaled to perform multi-analyte detection, unlike single CNT devices that are challenging to fabricate and functionalize.

Having simple biosensor technology may permit wider use of biosensors. Existing technologies are relatively complex, have relatively limited capability for multi-analyte detection, and are costly. The BSC proposed here overcomes each of these limitations. BSCs are very simple to fabricate and to operate and are capable of multi-analyte detection. Using BSCs, it is possible to fabricate miniaturized "Biological Central Processing Units (CPUs)" with multiple biological elements, capable of processing and sorting out information on multiple analytes simultaneously. By combining them with computer algorithms, it is possible to automatically perform multi-analyte detection and make decisions analogous to the way a silicon chip processes digital information to make decisions important for direct biodetection of multiple microbial pathogens and their toxins, numerous cancer biomarkers, cardiovascular or kidney biomarkers.

Example 2

Fabrication of the Gate Region

Materials and Reagents:

Staphylococcal enterotoxin B (SEB), rabbit anti-SEB affinity purified IgG, and peroxidase (HRP) conjugated anti-SEB IgG were purchased from Toxin Technology (Sarasota, Fla.). Single-walled Carbon Nanotubes (CNTs) were obtained from Carbon Solutions Inc (Riverside, Calif.). Poly (diallyldimethylammonium chloride) polymer (PDDA) was purchased from Sigma-Aldrich (St. Louis, Mo.). Silver contact "Silver Liquid" was purchased from Electron Microscopy Sciences (Hatfield, Pa.). For ECL detection, Immun-Star HRP Chemiluminescence Kit was obtained from Bio-Rad (Hercules, Calif.). All other reagents were of analytical grade and de-ionized water was used throughout.

Fabrication of BSC Sensor:

The BSC sensor was designed in CorelDraw11 (Corel Corp. Ontario, Canada) and micro-machined in 1.5 mm acrylic using a computer controlled laser cutter Epilog Legend CO2 65W cutter (Epilog, Golden, Colo.). Before engraving the common electrode for all sixteen BSCs, the connection well for the readout electrode and cutting the slots for the bio-nanocomposite material, the lower side of the PMMA sheet was coated with 3M 9770 adhesive transfer doublesided tape (Piedmont Plastics, Beltsville, Md.) and the polycarbonate film was immobilized directly on the PMMA. The bio-nanocomposite was bonded to the polycarbonate film and the electrodes were filled with silver conducting paste.

Carbon Nanotube Preparation:

The CNTs (30 mg) were first shortened and oxidized by mixing with concentrated sulfuric acid and nitric acid mixture (3:1 v/v) and sonicating with a Fisher (FS-14) sonicator for 6 h followed by extensive washing in water (100 ml) until neutralized (pH 7.0). Then the CNT were dispersed in 100 ml 1M NaOH solution for 5 min to achieve net negative charged carboxylic acid groups and washed with water (100 ml).

CNT Functionalization:

a linker molecule to the carbon nanotube was used to attach the capture biomolecule. Poly(diallyldimethylammonium chloride (PDDA) is positively charged and SEB antibody was negatively charged, so antibodies electrostatically adsorbed onto carbon nanotube. The positively charged polycation was adsorbed by dispersing the CNT in 50 ml of 1 mg/mL PDDA containing 0.5 M NaCl for 30 min followed by centrifugation (10,000 RPM in Beckman centrifuge for 15 minutes) and washed with 100 ml of water.

CNT-Antibody Complex Preparation:

The CNT were functionalized by dispersing in a rabbit anti-SEB IgG phosphate buffer solution (20 mM, pH 8.0) at a concentration of 0.01 mg/mL for 1 h at room temperature, so that the antibody was adsorbed onto the CNT surface. After centrifugation (15 minutes) and washing extensively with water (10 ml), the modified CNT was stored at 4° C. in pH 8.0 phosphate buffer at a concentration of approximately 1 mg/mL for no more than two weeks before use.

BSC Detection of SEB:

The CNT-antibody complex described above is immobilized directly on polycarbonate. Before applying SEB samples, the resistance of the BSC is first measured ($R_0$). Different concentrations of SEB samples in phosphate buffer are added to sample wells and incubated for 60 min at room temperature (25° C.). After washing, the BSC was dried at room temperature for 2 hours and the resistance measured again ($R_1$). The difference between the two readings ($R_1-R_0$) is used as signal corresponding to different concentration of SEB.

SEB Detection Using ECL:

For the control experiment, after SEB binding, the BSC was then blocked with 1% BSA in 15 μl buffer for 30 min. A HRP conjugated anti-rabbit IgG was added to the captured SEB and after 60 minutes incubation and washing, ECL was achieved by adding 7 mL of ECL buffer (formed by mixing the two solutions from the chemiluminescent kit in a 1:1 volume ratio) into each well and the ECL intensity was measured immediately with a custom-built point-of-care CCD detector. The CCD-based detector consists of an SXVF-M7.cooled CCD camera (Adirondack Video Astronomy, Hudson Falls, N.Y.) equipped with a 5 mm extension tube and a 12 mmPentax f1.2 lens (Spytown, Utopia, N.Y.). The luminescence was measured after 2 and 10 minutes of exposure. The CCD image intensities were analyzed using ImageJ software, developed and distributed freely by the NIH, and the data generated was then imported into Microsoft Excel for further manipulation.

Example 3

Food Sample Analysis

Food Sample Spiking:

To spike samples of soy milk, 1 mL of sample was transferred directly to a 2 mL centrifuge tube and different concentrations of SEB were added.

Cation Exchanger Carboxymethylcellulose (CM) for Partial Sample Purification:

To detect SEB in food samples, partial sample purification was used to help reduce assay background by reducing cross-reaction of the antibodies with other components of the food matrix. In order to establish a widely applicable assay for different foods, the new SWNT-EL immunoassay method was tested in food samples with and without partial toxin purification using the cation exchanger carboxymethylcellulose (Clvl). To prepare eM for approximately 100 purification assays, 1 g of eM was equilibrated with 20 mL loading buffer (loading buffer=5 mM NaP03, pH 5.7) until the gel was swollen and then centrifuged at 4000 rrnp for 2 min. After centrifugation, the gel was allowed to settle, the buffer was removed and the Cvl was washed twice with 20 ml of loading buffer followed by centrifugation as above. After the removal of the buffer in the last centrifugation, loading buffer was added to a final volume of 20 mL. The equilibrated Clvl was stored at 4 "c before use.

Sample Preparation:

The tubes containing the spiked food samples were vortexed briefly, centrifuged at 14,000 rpm for 2 min, and the resulting supernatant transferred into a fresh tube. Loading buffer was added into the supernatant to reach a sample volume of I mL. The sample (400 J.1L) was mixed with 200 J.1L of equilibrated eM, and vortexed for 30 min. which was following by centrifugation at 14,000 rpm for 2 min and the soluble material was removed. The material left at the tube was then washed 3 times by repeatedly adding loading buffer and centrifuging. Finally, 100 J.1L elution buffer (50 mM aP03, pH 6.5; 50 mM NaCl) was added to the matrix, the tubes centrifuged and eluted material collected for immunoassay.

The semiconductor sensor used (See FIG. 11) is a unipolar device, with two electrodes on both side of the SWNT-antibody resistor printed on a PMMA surface. Several BSCs can be printed on the same PMMA surface. At the circuit level, semiconductor operation is simple: the current flow through the BSC gate via the source and drain electrodes and the application of the specific antigen into the gate controls the resistance of the semiconductor, which is measured by an ohm meter via the electrodes.

The biological nanocomposite sensor acts as a semiconductor with a variable gate with an ON mode and with a constant current flow between the source and drain. Upon actuation by binding of antigen to the antibody on the gate (FIG. 11B), the current flow changes with the change of resistance of the semiconductor. Such change in conductivity (the variable OFF mode) depends on the amount of antigens bound.

Figure 11C:
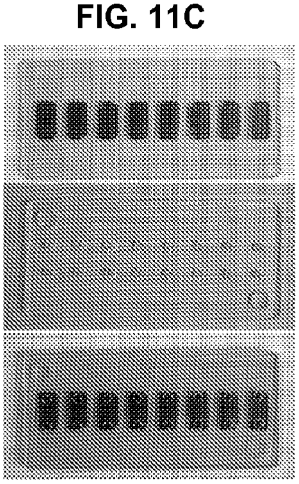
Figure 11B:
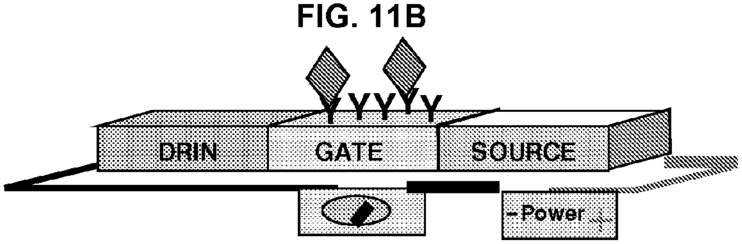

A simplified prototype of the semiconductor sensor is shown in FIG. 11C. The rabbit anti-SEB IgG-functionalized SWNT gate was immobilized into the PMMA circuit board fabricated with laser micromachining. A previously developed CNT functionalization scheme was used in which shortened (by sonication) and oxidized CNT (reacted with concentrated sulfuric acid and nitric acid mixture) were dispersed in NaOH solution to achieve net negative charged carboxylic acid groups which then absorb a linker molecule Poly(diallyldimethylammonium chloride (PDDA) which is positively charged. The activated CNT was then reacted with rabbit anti-SEB IgG which are negatively charged, so antibodies electro statically adsorbed onto carbon nanotube.

The circuit board with eight such semiconductors was then used for conventional immunodetection assay including binding of SEB to the gate and washing unbound material. A second layer of PMMA with holes for the source and the drain electrodes (FIG. 11C, middle portion) was used to seal the eight BSC sensor chip. The assembled chip is shown in FIG. 11C, bottom. For SEB measurement, the source and the drain electrodes were inserted into the holes to measure change in resistance upon actuation by SEB. The measurement value was calculated as the difference between the initial reading recorded (Rn) with no SEB and the reading with SEB (Rr). The difference between the two reading was used as signal corresponding to different concentration of SEB.

Figure 12A:
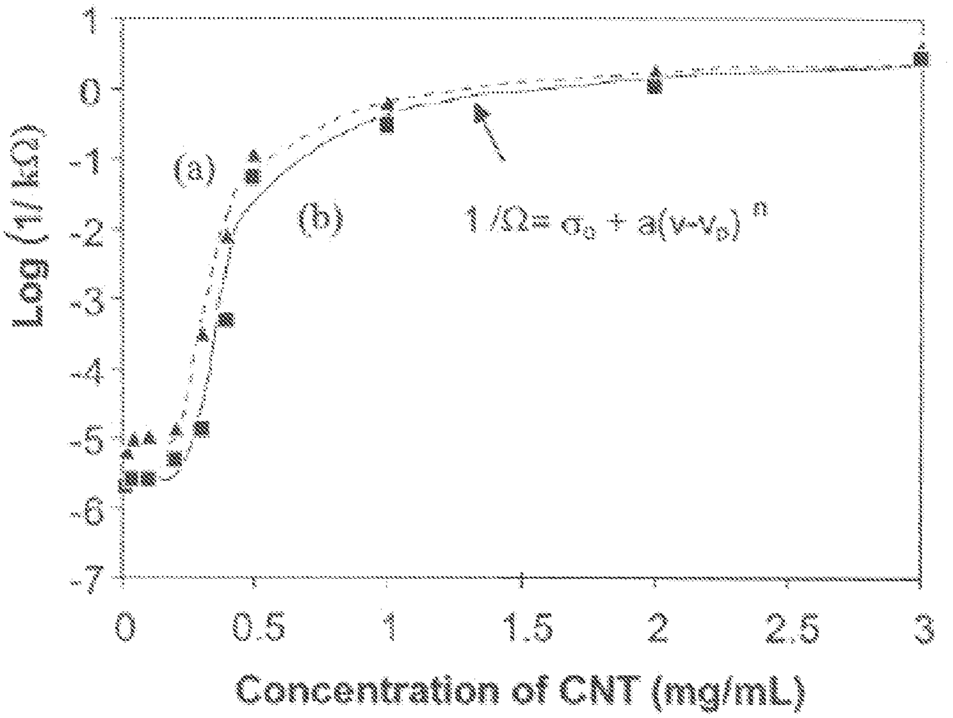
FIGS. 12A and 12B illustrate percolation curves of a single-walled carbon nanotube according to another example.

SWNT-Antibody Percolation Curve:

For establishing SWNT-antibody percolation curve, various concentrations of SWNT (FIG. 12A, labeled as (a)) and SWNT film immobilized with primary antibody (FIG. 12A, labeled as (b)) were immobilized on PMMA at various SWNT concentrations, v, and their resistance, Q, was measured to determine the percolation threshold, vP' using a conventional power law equation. The percolation threshold for SWNT is between 0.2 to 0.3 mg/mL (FIG. 2A a), while after antibody immobilized, the threshold shifted to between 0.3 and 0.4 mg/mL, reducing the base conductivity, σ, by ⅓rd and increasing the exponent, n, from 8 to 9 while shifting the percolation threshold from 0.2 to 0.22.

The percolation threshold of the SWNT-antibody indicates that the typical resistance of the will be higher than the resistance is attributed to the SWNT, presumably due to the contacts between the antibody and the SWNT in the functionalized SWNT. The change in resistance as the SWNTs percolate is approximately 5 orders of magnitude. For irnmunodetection, the SWNT film was prepared with 1 mg/mL of SWNT, which has a resistance of around 1 kO, and corresponds to the point at which the change in resistance begins to level off, consistent with the complete percolation of the SWNTs. For the detection of SEB, after the antibody is immobilized and the BSA blocked, the resistance increased to about 5 kO. Thus, this 1 mg/mL of SWNT should provide the greatest sensitivity to the increase in resistance due to SEB.

Figure 12B:
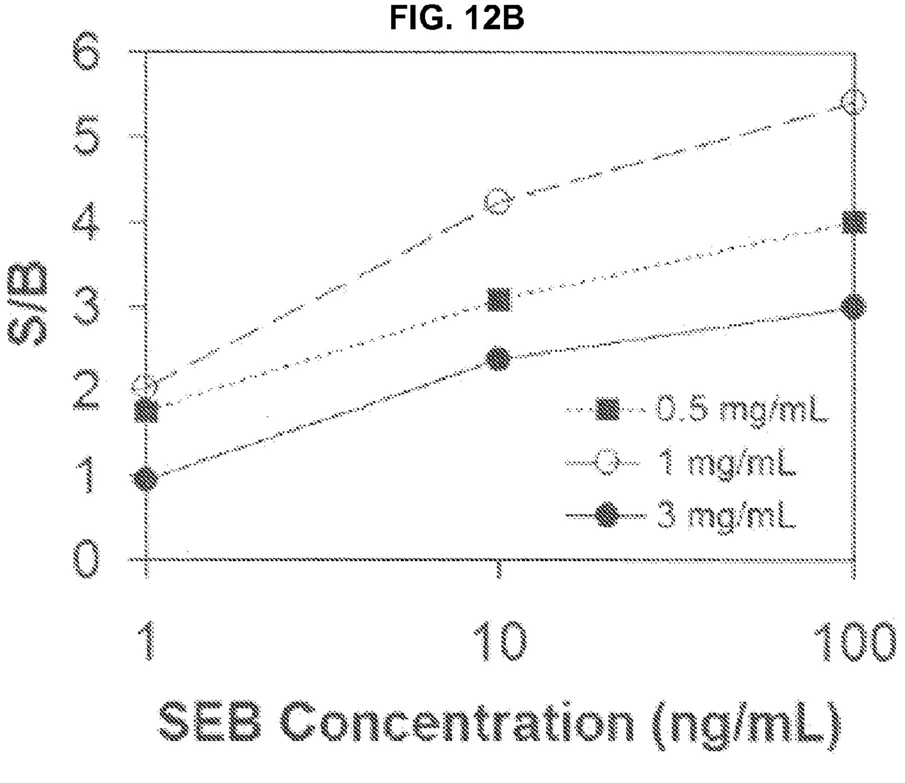

Electrical Percolation Biological Semiconductor Immunosensor:

The highest sensitivity to SEB for the immunosensor is around 1 mg/mL SWNT (FIG. 12(B)), which is the point at which the percolation is complete and subsequent increases correspond to the increase in SWNT concentration. This level is determined by the amount of antibody immobilized on the SWNTs, which will affect the sensitivity. Upon actuation by SEB, the resistance increases, e.g. for the detection of I ng/mL SEB, resistance change is about O.5K oluns. When various amounts of SEB (50, 10, 5,1, 0.1, 0.5, 0.01, ng/mL as well as the baseline at ° ng/mL) in buffer were added to the chip (FIG. 13), the resistance increased proportionally to the amount of SEB. To produce a calibration curve, a quadratic logarithmic fit was applied and was found to be the best for the log of SEB concentration. The log fit indicates a LOD that is –0.01 ng/mL, which is similar to typical levels of detection for commercial colorimetric ELISA systems which is from 0.5 to 2 ng/gr of food (16, 18-20, 25, 27). For determining the reproducibility of the measurements, eight samples of 1 ng/ml, SEB were analyzed and the RSD was 10.5%.

Figure 13:
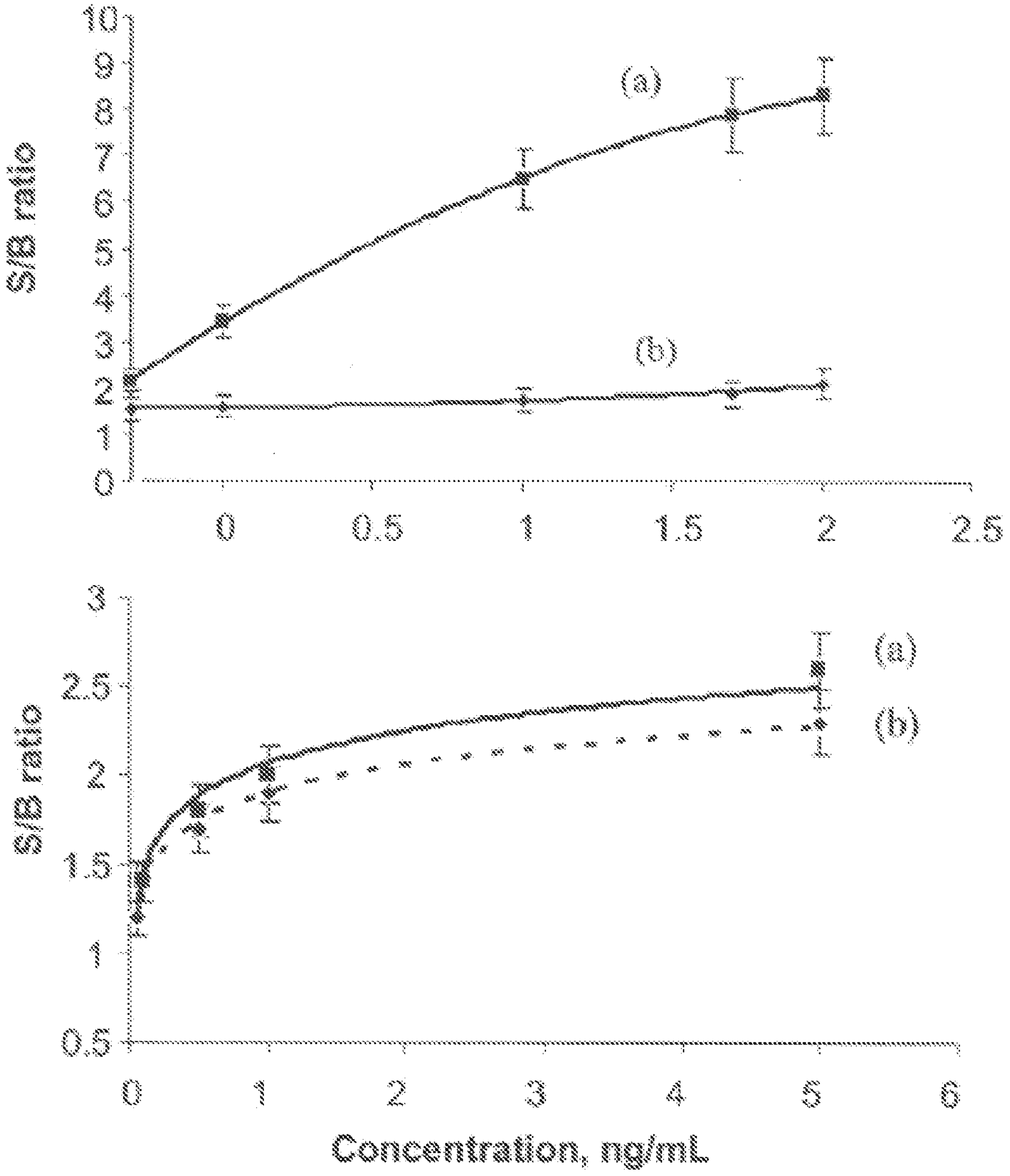
FIG. 13 shows electrical characteristics of staphylococcal enterotoxin B (SEB) actuation of a semiconductor according to another example.

To study the BSC leak rate, which is the change in resistance with non-specific binding and is an indication of the specificity and the selectivity of BSC actuation, high concentrations of none specific antigens including smaller molecular weight (14 kDa) protein lysozyme (FIG. 13B, labeled (a)) and higher MW protein human IgO which is 150 kDa protein were used to actuate the chip. In this experiment, high concentrations of the non-specific antigens (e.g. up to 50 ng/ml) were used to measure the leak rate. As shown in FIG. 13, the level of non-specific leak rate in these semiconductors is small and can be used to define the BSC limit of detection.

Figure 14:
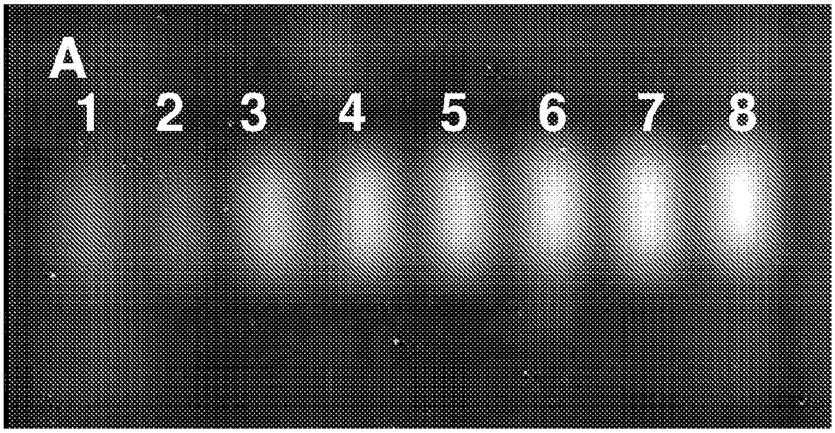
FIG. 14 shows that quantitative measurements in FIG. 13 correspond to traditional quantitative measurement methods using labeling and optical sensing assay analysis of captured SEB on a semiconductor chip, according to a second example.
Figure 14:
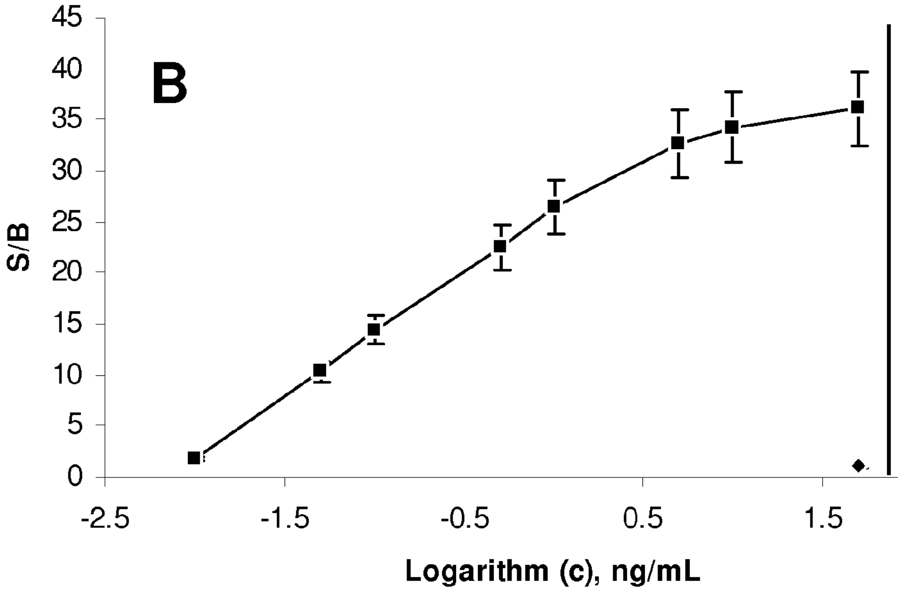
Figure 14:
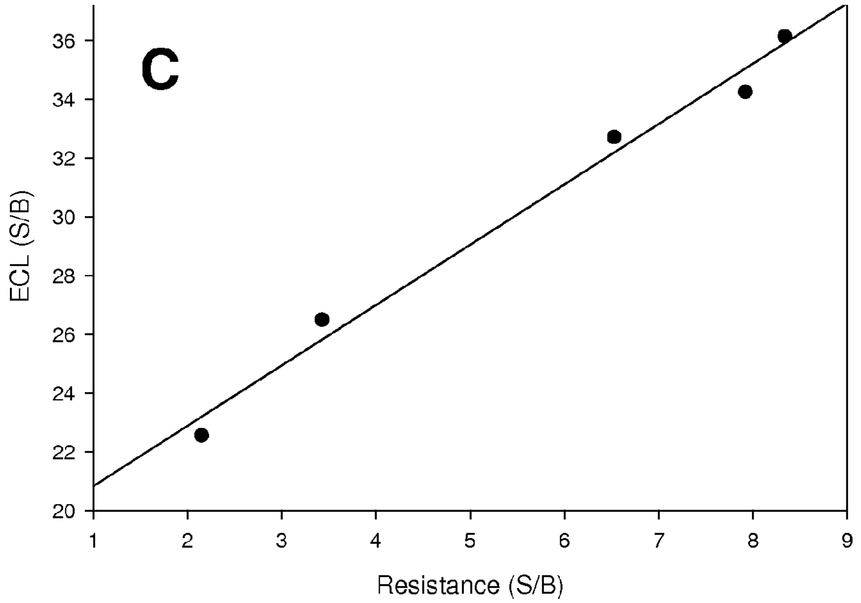

Sandwich Assay Analysis of Captured SEB on WPBS Chip:

To further analyze the electric signal shown in FIG. 14, SEB captured on the BSC by a sandwich immunoassay was measured. The chip with the captured SEB incubated with different concentrations of SEB was washed (2 ml phosphate buffer), and the immunosensor coated with antibody-antigen complex was exposed to Horseradish Peroxidase (HRP) conjugated anti-SEB IgO (15 J1L, 0.01 mg/mL) in buffer for 1 h followed by 3 cycles of washing with 2 ml of phosphate buffer. HRP was assayed with ECL by adding 7 ul. of ECL buffer (mix the two solutions from Chemiluminescent Kit in a 1:1 volume ratio) into each well and the ECL intensity was measured immediately with a custom-built Point-of-Care CCO detector described in previous work. The luminescence was measured over the full optical spectrum after 20 minutes of exposure. The CCO Image intensities were analyzed using ImageJ software, and the data generated is then analyzed using a concentration of 0 ng/mL SEB as background. The ratio of the signal to background (S/B) ratio was further used to quantify the SEB concentration. The intensity of the signal from the captured SEB on the BSC chip is proportional to the amount of SEB. Quantitative analysis of the data (FIG. 14B) suggest a high correlation between the amount of SEB and the ECL signal and that there is a very high correlation (r2=0.9996) between the electric measurements (FIG. 13) and the ECL measurements The linear regression (Y=18.774S+2.0556X) is highly significant (P<O.002) suggesting that indeed the anti SEB 109 on the BSC chip indeed captured SEB and that the direct electrical measures are in agreement with the indirect sandwich immunoassay.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A semiconductor, comprising:

first and second electrodes; and a gate region between the first and second electrodes, the gate region including a three-dimensional matrix of electrical conductors, wherein multiple of the electrical conductors have capture biomolecules bound thereto within the matrix that disrupt the three-dimensional matrix of electrical conductors when the capture biomolecules bind to a target molecule, wherein the disruption causes at least some of the electrical conductors between the first and second electrodes to be severed;

the matrix of electrical conductors having a modifiable resistivity, impedance or capacitance related to molecular binding between the capture biomolecules and target molecules.

2. The semiconductor of claim 1, wherein the capture biomolecules include one or more of the following: antibodies, nucleic acid molecules such as DNA or RNA, peptides such as receptors, enzymes or aptamers.

3. The semiconductor of claim 1, wherein the electrical conductors in the three-dimensional matrix are unstructured and are randomly interconnected.

4. The semiconductor of claim 1, wherein the three-dimensional matrix is formed from a plurality of single-walled nanotubes, or nanowires made of metal, such as gold or silver, or conductive polymers, such as polypyrolle and polythiophene.

5. The semiconductor of claim 1, further including a substrate and wherein the electrical conductors are bound to a surface of the substrate to allow movement of the conductors in response to molecular binding.

6. The semiconductor of claim 1, wherein electrical conductivity, capacitance or impedance of the gate region is based on electrical percolation and the gate region is substantially near a percolation threshold.

7. The semiconductor of claim 1, wherein the matrix includes a multilayer, three-dimensional network formed from one or more of the following: carbon nanotubes, graphene, and buckyballs, metal nanowires and nanowires made from conducting polymers.

8. The semiconductor of claim 1, wherein the capture biomolecules bind with the target molecules to create a specific binding pair, which is selected from a group of the following: antigens and antibodies, nucleic acid molecules, and hormone and receptor.

9. The semiconductor of claim 1, wherein the electrical conductors are nanotubes and further including shielding the nanotubes from the environment using a layer of polydiallyldimethylammonium chloride.

10. The semiconductor of claim 1, wherein the matrix of electrical conductors is formed by carbon nanotubes and wherein the molecular binding reduces the number of contacts between the carbon nanotubes in the matrix.

11. The semiconductor of claim 1, wherein the first and second electrodes and the gate form a transistor.

12. The semiconductor of claim 1, wherein the resistivity, capacitance or impedance of the biological semiconductor can be read using the first and second electrodes.

13. The semiconductor of claim 1, wherein conductivity of the matrix is based on electrical percolation.

14. A circuit coupled to the semiconductor of claim 1 for measuring resistance across the semiconductor.

15. A method of detecting molecular interactions in a semiconductor, comprising:

providing the semiconductor, the semiconductor including:

(a) first and second electrodes; and (b) a gate region between the first and second electrodes, the gate region including a three-dimensional matrix of electrical conductors, wherein multiple of the electrical conductors have capture biomolecules bound thereto within the matrix that disrupt the three-dimensional matrix of electrical conductors when the capture biomolecules bind to a target molecule;

(c) the matrix of electrical conductors having a modifiable resistivity, impedance or capacitance related to molecular binding between the capture biomolecules and target molecules;

applying a specimen including target molecules to be detected by the semiconductor;

automatically measuring resistance between the first and second electrodes in order to detect whether the target molecules are bound with the capture biomolecules.

16. The method of claim 15, further including automatically comparing the measured resistance to a control resistance to determine a quantity of the target molecules that are bound with the capture biomolecules.

17. The method of claim 15, wherein automatically measuring resistance includes coupling an ohm meter between the first and second electrodes.

18. The method of claim 15, further including automatically injecting the specimen into the gate region and automatically detecting whether target molecules of interest are in the specimen.

19. A system for detecting molecular interactions, comprising:

a semiconductor comprising the following:

(a) first and second electrodes; and (b) a gate region between the first and second electrodes, the gate region including a three-dimensional matrix of electrical conductors, wherein multiple of the electrical conductors have capture biomolecules bound thereto within the matrix that disrupt the three-dimensional matrix of electrical conductors when the capture biomolecules bind to a target molecule;

(c) the matrix of electrical conductors having a modifiable resistivity, impedance or capacitance related to molecular binding between the capture biomolecules and target molecules;

a resistivity measurement device coupled to the first and second electrodes;

a computer coupled to the resistivity measurement device for automatically and continuously monitoring resistivity;

a plurality of valves controlling different specimens to be supplied to the gate region of the semiconductor, the plurality of valves coupled to the computer, which automatically controls the valves to release one or more specimens to the gate region.

20. The system of claim 19, wherein the resistivity measurement device is an Ohm meter.

21. The system of claim 19, wherein the capture biomolecules include one or more of the following: antibodies, nucleic acid molecules, enzymes, aptamers, and peptides.

22. The system of claim 19, wherein the matrix of electrical conductors is formed by bio-nanocarbon material interconnected in a random, unpatterned fashion.

23. The system of claim 22, wherein the bio-nanocarbon material includes a plurality of single-walled nanotubes.

24. The system of claim 19, further including a pump positioned between the plurality of valves and the semiconductor.

25. The system of claim 19, further including a digital-to-analog converter positioned between the plurality of valves and the computer to facilitate communication therebetween.

26. The system of claim 19, wherein the matrix is a multilayer, three-dimensional network formed from one or more of the following: carbon nanotubes, graphene, and buckyballs.

27. The system of claim 19, wherein the capture biomolecules bind with the target molecules to create a binding pair, which is selected from a group of the following: antigens and antibodies, nucleic acid molecules, and hormone and receptor.

28. A method of manufacturing a semiconductor, comprising:

providing a multi-layered material capable of forming a matrix of electrical conductors, which are severable when capture biomolecules coupled to the electrical conductors bind to target molecules;

immobilizing capture biomolecules onto surfaces of the electrical conductors through electrostatic absorption to form a solution;

form a gate region of the semiconductor by depositing the solution into a well region; and after the gate region has been formed, depositing electrode material at opposing ends of the gate region.

29. The method of claim 28, wherein the gate region is formed on a non-conductive substrate.

30. The method of claim 28, further including forming multiple semiconductors in parallel by coupling electrodes at one of the opposing ends together to form a common.

* * * * *